US011815860B2

United States Patent
Pandya et al.

(10) Patent No.: US 11,815,860 B2
(45) Date of Patent: *Nov. 14, 2023

(54) SWITCH MODULE FOR ELECTRONIC CROWN ASSEMBLY

(71) Applicant: Apple Inc., Cupertino, CA (US)

(72) Inventors: Sameer Pandya, Sunnyvale, CA (US); Antonio Herrera, Woodside, CA (US); Colin M Ely, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/989,057

(22) Filed: Nov. 17, 2022

(65) Prior Publication Data
US 2023/0077241 A1    Mar. 9, 2023

Related U.S. Application Data

(63) Continuation of application No. 16/890,880, filed on Jun. 2, 2020, now Pat. No. 11,550,268.

(51) Int. Cl.
*G04C 11/00* (2006.01)
*G04C 3/00* (2006.01)
(Continued)

(52) U.S. Cl.
CPC .............. *G04C 3/002* (2013.01); *A61B 5/332* (2021.01); *A61B 5/681* (2013.01); *G04G 21/025* (2013.01);
(Continued)

(58) Field of Classification Search
CPC ......... G04C 3/002; A61B 5/332; A61B 5/681; A61B 5/282; A61B 5/02438;
(Continued)

(56) References Cited

U.S. PATENT DOCUMENTS 2,237,860 A    4/1941   Bolle
2,288,215 A    6/1942   Taubert et al.
(Continued)

FOREIGN PATENT DOCUMENTS

CH    1888928    1/1937
CN    1302740    9/2001
(Continued)

OTHER PUBLICATIONS

Author Unknown, "Desirable Android Wear smartwatch from LG," Gulf News, Dubai, 3 pages, Jan. 30, 2015.
(Continued)

*Primary Examiner* — Thuy N Pardo
(74) *Attorney, Agent, or Firm* — Brownstein Hyatt Farber Schreck, LLP

(57) ABSTRACT

A switch module for an electronic device detects translational inputs and defines at least portion of a conductive path from an input surface of the electronic device to a processing unit of the electronic device. The switch module may be a component of a crown assembly for detecting rotational inputs, translational inputs, touch inputs and/or biological signals such as electrocardiogram (ECG) signals. The switch module may include a conductive dome and a friction guard that is positioned between the conductive dome and the actuation member of the crown assembly. The conductive dome and/or the friction guard may define at least a portion of the conductive path from the input surface to the processing unit.

20 Claims, 19 Drawing Sheets

(51) Int. Cl.
  *H05K 5/00* (2006.01)
  *H05K 5/02* (2006.01)
  *H01H 19/14* (2006.01)
  *A61B 5/00* (2006.01)
  *G04G 21/02* (2010.01)
  *G04G 21/08* (2010.01)
  *H01H 19/08* (2006.01)
  *A61B 5/332* (2021.01)

(52) U.S. Cl.
  CPC .............. *G04G 21/08* (2013.01); *H01H 19/08* (2013.01); *H01H 19/14* (2013.01); *H05K 5/0017* (2013.01); *H05K 5/0217* (2013.01)

(58) Field of Classification Search
  CPC .... A61B 5/0245; G04G 21/025; G04G 21/08; H01H 19/08; H01H 19/14; H01H 25/06; H01H 2231/028; H05K 5/0017; H05K 5/0217; G06F 1/1671; G06F 1/169; G06F 3/0312; G06F 3/0383; G06F 1/163
  USPC .................. 345/8, 9, 169; 368/10, 46, 61
  See application file for complete search history.

(56) References Cited

U.S. PATENT DOCUMENTS

| | | |
|---|---|---|
| 2,497,935 A | 2/1950 | Feurer |
| 2,771,734 A | 11/1956 | Morf |
| 2,788,236 A | 4/1957 | Kafowi |
| 2,797,592 A | 7/1957 | Marrapese |
| 3,040,514 A | 6/1962 | Dinstman |
| 3,056,030 A | 9/1962 | Kelchner |
| 3,130,539 A | 4/1964 | Davis |
| 3,355,873 A | 12/1967 | Morf |
| 3,362,154 A | 1/1968 | Perret |
| 3,410,247 A | 11/1968 | Dronberger |
| 3,495,398 A | 2/1970 | Widmer et al. |
| 3,577,876 A | 5/1971 | Spadini |
| 3,621,649 A | 11/1971 | Vulcan et al. |
| 3,662,618 A | 5/1972 | Kroll et al. |
| 3,733,803 A | 5/1973 | Hiraga |
| 3,937,002 A | 2/1976 | Haften |
| 4,007,347 A | 2/1977 | Haber |
| 4,031,341 A | 6/1977 | Wuthrich et al. |
| 4,037,068 A | 7/1977 | Gaynor |
| 4,051,665 A | 10/1977 | Arn |
| 4,077,200 A | 3/1978 | Schneider |
| 4,133,404 A | 1/1979 | Griffin |
| 4,170,104 A | 10/1979 | Yamagata |
| 4,258,096 A | 3/1981 | LaMarche |
| 4,274,152 A | 6/1981 | Ikegami |
| 4,287,400 A | 9/1981 | Kitik |
| 4,289,400 A | 9/1981 | Kubola et al. |
| 4,311,026 A | 1/1982 | Ochoa |
| 4,311,990 A | 1/1982 | Burke |
| 4,324,956 A | 4/1982 | Sakakino et al. |
| 4,345,119 A | 8/1982 | Latasiewicz |
| 4,364,674 A | 12/1982 | Tesch |
| 4,379,642 A | 4/1983 | Meyrat |
| 4,395,134 A | 7/1983 | Luce |
| 4,396,298 A | 8/1983 | Ripley |
| 4,417,824 A | 11/1983 | Paterson et al. |
| 4,448,199 A | 5/1984 | Schmid |
| 4,520,306 A | 5/1985 | Kirby |
| 4,581,509 A | 4/1986 | Sanford et al. |
| 4,600,316 A | 7/1986 | Besson |
| 4,617,461 A | 10/1986 | Subbarao et al. |
| 4,634,861 A | 1/1987 | Ching et al. |
| 4,641,026 A | 2/1987 | Garcia, Jr. |
| 4,670,737 A | 6/1987 | Rilling |
| 4,766,642 A | 8/1988 | Gaffney et al. |
| 4,783,772 A | 11/1988 | Umemoto et al. |
| 4,884,073 A | 11/1989 | Souloumiac |
| 4,914,831 A | 4/1990 | Kanezashi et al. |
| 4,922,070 A | 5/1990 | Dorkinski |
| 4,931,794 A | 6/1990 | Haag |
| 4,952,799 A | 8/1990 | Loewen |
| 4,980,685 A | 12/1990 | Souloumiac et al. |
| 4,987,299 A | 1/1991 | Kobayashi et al. |
| 5,034,602 A | 7/1991 | Garcia et al. |
| 5,177,355 A | 1/1993 | Branan |
| 5,214,278 A | 5/1993 | Banda |
| 5,258,592 A | 11/1993 | Nishikawa et al. |
| 5,288,993 A | 2/1994 | Bidiville et al. |
| 5,347,123 A | 9/1994 | Jackson et al. |
| 5,383,166 A | 1/1995 | Gallay |
| 5,471,054 A | 11/1995 | Watanabe |
| 5,477,508 A | 12/1995 | Will |
| 5,509,174 A | 4/1996 | Worrell |
| 5,559,761 A | 9/1996 | Frenkel et al. |
| 5,572,314 A | 11/1996 | Hyman et al. |
| 5,583,560 A | 12/1996 | Florin et al. |
| 5,631,881 A | 5/1997 | Pessey et al. |
| 5,726,645 A | 3/1998 | Kamon et al. |
| 5,738,104 A | 4/1998 | Lo |
| 5,748,111 A | 5/1998 | Bates |
| 5,825,353 A | 10/1998 | Will |
| 5,841,050 A | 11/1998 | Clift et al. |
| 5,847,335 A | 12/1998 | Sugahara et al. |
| 5,867,082 A | 2/1999 | Van Zeeland |
| 5,943,233 A | 8/1999 | Ebina |
| 5,953,001 A | 9/1999 | Challener et al. |
| 5,960,366 A | 9/1999 | Duwaer et al. |
| 5,963,332 A | 10/1999 | Feldman et al. |
| 5,999,168 A | 12/1999 | Rosenberg et al. |
| 6,069,567 A | 5/2000 | Zawilski |
| 6,128,006 A | 10/2000 | Rosenberg et al. |
| 6,134,189 A | 10/2000 | Carrard |
| 6,154,201 A | 11/2000 | Levin et al. |
| 6,175,679 B1 | 1/2001 | Veligdan et al. |
| 6,203,190 B1 | 3/2001 | Stotz |
| 6,241,684 B1 | 6/2001 | Amano |
| 6,246,050 B1 | 6/2001 | Tullis et al. |
| 6,252,825 B1 | 6/2001 | Perotto |
| 6,304,247 B1 | 10/2001 | Black |
| 6,355,891 B1 | 3/2002 | Ikunami |
| 6,361,502 B1 | 3/2002 | Puolakanaho et al. |
| 6,377,239 B1 | 4/2002 | Isikawa |
| 6,392,640 B1 | 5/2002 | Will |
| 6,396,006 B1 | 5/2002 | Yokoji et al. |
| 6,422,740 B1 | 7/2002 | Leuenberger |
| 6,477,117 B1 | 11/2002 | Narayanaswami et al. |
| 6,502,982 B1 | 1/2003 | Bach et al. |
| 6,525,278 B2 | 2/2003 | Villain et al. |
| 6,556,222 B1 | 4/2003 | Narayanaswami |
| 6,575,618 B1 | 6/2003 | Inoue et al. |
| 6,587,400 B1 | 7/2003 | Line |
| 6,636,197 B1 | 10/2003 | Goldenberg et al. |
| 6,646,635 B2 | 11/2003 | Pogatetz et al. |
| 6,661,438 B1 | 11/2003 | Shiraishi et al. |
| 6,672,758 B2 | 1/2004 | Ehrsam et al. |
| 6,794,992 B1 | 9/2004 | Rogers |
| 6,809,275 B1 | 10/2004 | Cheng et al. |
| 6,834,430 B2 | 12/2004 | Worrell |
| 6,846,998 B2 | 1/2005 | Hasumi et al. |
| 6,882,596 B2 | 4/2005 | Guanter |
| 6,888,076 B2 | 5/2005 | Hetherington |
| 6,896,403 B1 | 5/2005 | Gau |
| 6,909,378 B1 | 6/2005 | Lambrechts et al. |
| 6,914,551 B2 | 7/2005 | Vidal |
| 6,950,695 B2 | 9/2005 | Chen |
| 6,961,099 B2 | 11/2005 | Takano et al. |
| 6,963,039 B1 | 11/2005 | Weng et al. |
| 6,967,903 B2 | 11/2005 | Guanter |
| 6,977,868 B2 | 12/2005 | Brewer et al. |
| 6,982,930 B1 | 1/2006 | Hung |
| 6,985,107 B2 | 1/2006 | Anson |
| 6,987,568 B2 | 1/2006 | Dana |
| 6,998,553 B2 | 2/2006 | Hisamune et al. |
| 7,009,915 B2 | 3/2006 | Brewer et al. |
| 7,016,263 B2 | 3/2006 | Gueissaz et al. |
| 7,021,442 B2 | 4/2006 | Borgerson |
| 7,031,228 B2 | 4/2006 | Born et al. |

(56) References Cited

U.S. PATENT DOCUMENTS

| | | |
|---|---|---|
| 7,034,237 B2 | 4/2006 | Ferri et al. |
| 7,081,905 B1 | 7/2006 | Raghunath et al. |
| 7,102,626 B2 | 9/2006 | Denny, III |
| 7,111,365 B1 | 9/2006 | Howie, Jr. |
| 7,113,450 B2 | 9/2006 | Plancon et al. |
| 7,119,289 B2 | 10/2006 | Lacroix |
| 7,135,673 B2 | 11/2006 | Saint Clair |
| 7,167,083 B2 | 1/2007 | Giles |
| 7,187,359 B2 | 3/2007 | Numata |
| 7,244,927 B2 | 7/2007 | Huynh |
| 7,255,473 B2 | 8/2007 | Hiranuma et al. |
| 7,265,336 B2 | 9/2007 | Hataguchi et al. |
| 7,274,303 B2 | 9/2007 | Dresti et al. |
| 7,285,738 B2 | 10/2007 | Lavigne et al. |
| 7,286,063 B2 | 10/2007 | Gauthey |
| 7,292,741 B2 | 11/2007 | Ishiyama et al. |
| 7,358,481 B2 | 4/2008 | Yeoh et al. |
| 7,369,308 B2 | 5/2008 | Tsuruta et al. |
| 7,371,745 B2 | 5/2008 | Ebright et al. |
| 7,385,874 B2 | 6/2008 | Vuilleumier |
| 7,404,667 B2 | 7/2008 | Born et al. |
| 7,465,917 B2 | 12/2008 | Chin et al. |
| 7,468,036 B1 | 12/2008 | Rulkov et al. |
| 7,474,592 B2 | 1/2009 | Lyon |
| 7,506,269 B2 | 3/2009 | Lang et al. |
| 7,520,664 B2 | 4/2009 | Wai |
| 7,528,824 B2 | 5/2009 | Kong |
| 7,545,367 B2 | 6/2009 | Sunda et al. |
| 7,591,582 B2 | 9/2009 | Hiranuma et al. |
| 7,593,755 B2 | 9/2009 | Colando et al. |
| 7,605,846 B2 | 10/2009 | Watanabe |
| 7,634,263 B2 | 12/2009 | Louch et al. |
| 7,646,677 B2 | 1/2010 | Nakamura |
| 7,655,874 B2 | 2/2010 | Akieda |
| 7,682,070 B2 | 3/2010 | Burton |
| 7,708,457 B2 | 5/2010 | Girardin |
| 7,710,456 B2 | 5/2010 | Koshiba et al. |
| 7,732,724 B2 | 6/2010 | Otani et al. |
| 7,761,246 B2 | 7/2010 | Matsui |
| 7,763,819 B2 | 7/2010 | Ieda et al. |
| 7,772,507 B2 | 8/2010 | Orr |
| 7,778,115 B2 | 8/2010 | Ruchonnet |
| 7,781,726 B2 | 8/2010 | Matsui et al. |
| RE41,637 E | 9/2010 | O'Hara et al. |
| 7,791,587 B2 | 9/2010 | Kosugi |
| 7,791,588 B2 | 9/2010 | Tierling et al. |
| 7,791,597 B2 | 9/2010 | Silverstein et al. |
| 7,822,469 B2 | 10/2010 | Lo |
| 7,856,255 B2 | 12/2010 | Tsuchiya et al. |
| 7,858,583 B2 | 12/2010 | Schmidt et al. |
| 7,865,324 B2 | 1/2011 | Lindberg |
| 7,894,957 B2 | 2/2011 | Carlson |
| 7,946,758 B2 | 5/2011 | Mooring |
| 8,063,892 B2 | 11/2011 | Shahoian et al. |
| 8,138,488 B2 | 3/2012 | Grot |
| 8,143,981 B2 | 3/2012 | Washizu et al. |
| 8,167,126 B2 | 5/2012 | Stiehl |
| 8,169,402 B2 | 5/2012 | Shahoian et al. |
| 8,188,989 B2 | 5/2012 | Levin et al. |
| 8,195,313 B1 | 6/2012 | Fadell et al. |
| 8,229,535 B2 | 7/2012 | Mensinger et al. |
| 8,248,815 B2 | 8/2012 | Yang et al. |
| 8,263,886 B2 | 9/2012 | Lin et al. |
| 8,263,889 B2 | 9/2012 | Takahashi et al. |
| 8,275,327 B2 | 9/2012 | Yi et al. |
| 8,294,670 B2 | 10/2012 | Griffin et al. |
| 8,312,495 B2 | 11/2012 | Vanderhoff |
| 8,318,340 B2 | 11/2012 | Stimits |
| 8,368,677 B2 | 2/2013 | Yamamoto |
| 8,371,745 B2 | 2/2013 | Manni |
| 8,373,661 B2 | 2/2013 | Lan et al. |
| 8,405,618 B2 | 3/2013 | Colgate |
| 8,410,971 B2 | 4/2013 | Friedlander |
| 8,432,368 B2 | 4/2013 | Momeyer et al. |
| 8,439,559 B2 | 5/2013 | Luk et al. |
| 8,441,450 B2 | 5/2013 | Degner et al. |
| 8,446,713 B2 | 5/2013 | Lai |
| 8,456,430 B2 | 6/2013 | Oliver et al. |
| 8,477,118 B2 | 7/2013 | Lan et al. |
| 8,493,190 B2 | 7/2013 | Periquet et al. |
| 8,508,511 B2 | 8/2013 | Tanaka et al. |
| 8,525,777 B2 | 9/2013 | Stavely et al. |
| 8,562,489 B2 | 10/2013 | Burton et al. |
| 8,568,313 B2 | 10/2013 | Sadhu |
| 8,576,044 B2 | 11/2013 | Chapman |
| 8,593,598 B2 | 11/2013 | Chen et al. |
| 8,607,662 B2 | 12/2013 | Huang |
| 8,614,881 B2 | 12/2013 | Yoo |
| 8,666,682 B2 | 3/2014 | LaVigne et al. |
| 8,677,285 B2 | 3/2014 | Tsern et al. |
| 8,704,787 B2 | 4/2014 | Yamamoto |
| 8,711,093 B2 | 4/2014 | Ong et al. |
| 8,717,151 B2 | 5/2014 | Forutanpour et al. |
| 8,724,087 B2 | 5/2014 | Van De Kerkhof et al. |
| 8,730,167 B2 | 5/2014 | Ming et al. |
| 8,743,088 B2 | 6/2014 | Watanabe |
| 8,783,944 B2 | 7/2014 | Doi |
| 8,797,153 B2 | 8/2014 | Vanhelle et al. |
| 8,804,993 B2 | 8/2014 | Shukla et al. |
| 8,810,514 B2 | 8/2014 | Zhao et al. |
| 8,816,962 B2 | 8/2014 | Obermeyer et al. |
| 8,824,245 B2 | 9/2014 | Lau et al. |
| 8,847,741 B2 | 9/2014 | Birnbaum et al. |
| 8,851,372 B2 | 10/2014 | Zhou |
| 8,859,971 B2 | 10/2014 | Weber |
| 8,860,674 B2 | 10/2014 | Lee et al. |
| 8,863,219 B2 | 10/2014 | Brown et al. |
| D717,679 S | 11/2014 | Anderssen |
| 8,878,657 B2 | 11/2014 | Periquet et al. |
| 8,885,856 B2 | 11/2014 | Sacha |
| 8,895,911 B2 | 11/2014 | Takahashi |
| 8,905,631 B2 | 12/2014 | Sakurazawa et al. |
| 8,908,477 B2 | 12/2014 | Peters |
| 8,920,022 B2 | 12/2014 | Ishida et al. |
| 8,922,399 B2 | 12/2014 | Bajaj et al. |
| 8,928,452 B2 | 1/2015 | Kim et al. |
| 8,948,832 B2 | 2/2015 | Hong et al. |
| 8,954,135 B2 | 2/2015 | Yuen et al. |
| 8,975,543 B2 | 3/2015 | Hakemeyer |
| 8,994,827 B2 | 3/2015 | Mistry et al. |
| 9,001,625 B2 | 4/2015 | Essery et al. |
| 9,024,733 B2 | 5/2015 | Wouters |
| 9,028,134 B2 | 5/2015 | Koshoji et al. |
| 9,030,446 B2 | 5/2015 | Mistry et al. |
| 9,034,666 B2 | 5/2015 | Vaganov et al. |
| 9,039,614 B2 | 5/2015 | Yuen et al. |
| 9,041,663 B2 | 5/2015 | Westerman |
| 9,042,971 B2 | 5/2015 | Brumback et al. |
| 9,049,998 B2 | 6/2015 | Brumback et al. |
| 9,052,696 B2 | 6/2015 | Breuillot et al. |
| 9,086,717 B2 | 7/2015 | Meerovitsch |
| 9,086,738 B2 | 7/2015 | Leung et al. |
| 9,091,309 B2 | 7/2015 | Battlogg |
| 9,100,493 B1 | 8/2015 | Zhou |
| 9,101,184 B2 | 8/2015 | Wilson |
| 9,105,413 B2 | 8/2015 | Hiranuma et al. |
| 9,123,483 B2 | 9/2015 | Ferri et al. |
| 9,134,807 B2 | 9/2015 | Shaw et al. |
| 9,141,087 B2 | 9/2015 | Brown et al. |
| 9,176,577 B2 | 11/2015 | Jangaard et al. |
| 9,176,598 B2 | 11/2015 | Sweetser et al. |
| 9,202,372 B2 | 12/2015 | Reams et al. |
| 9,213,409 B2 | 12/2015 | Redelsheimer et al. |
| 9,223,296 B2 | 12/2015 | Yang et al. |
| 9,241,635 B2 | 1/2016 | Yuen et al. |
| 9,244,438 B2 | 1/2016 | Hoover et al. |
| 9,256,209 B2 | 2/2016 | Yang et al. |
| 9,277,156 B2 | 3/2016 | Bennett et al. |
| 9,350,850 B2 | 5/2016 | Pope et al. |
| 9,367,146 B2 | 6/2016 | Piot |
| 9,386,932 B2 | 7/2016 | Chatterjee et al. |
| 9,426,275 B2 | 8/2016 | Eim et al. |
| 9,430,042 B2 | 8/2016 | Levin |
| 9,437,357 B2 | 9/2016 | Furuki et al. |

(56) References Cited

U.S. PATENT DOCUMENTS

| | | |
|---|---|---|
| 9,449,770 B2 | 9/2016 | Sanford et al. |
| 9,501,044 B2 | 11/2016 | Jackson et al. |
| 9,520,100 B2 | 12/2016 | Houjou et al. |
| 9,532,723 B2 | 1/2017 | Kim |
| 9,542,016 B2 | 1/2017 | Armstrong-Muntner |
| 9,545,541 B2 | 1/2017 | Aragones et al. |
| 9,552,023 B2 | 1/2017 | Joo et al. |
| 9,599,964 B2 | 3/2017 | Gracia |
| 9,600,071 B2 | 3/2017 | Rothkopf |
| 9,606,721 B2 | 3/2017 | Park et al. |
| 9,607,505 B2 | 3/2017 | Rothkopf et al. |
| 9,620,312 B2 | 4/2017 | Ely et al. |
| 9,627,163 B2 | 4/2017 | Ely |
| 9,632,318 B2 | 4/2017 | Goto et al. |
| 9,632,537 B2 | 4/2017 | Memering |
| 9,638,587 B2 | 5/2017 | Marquas et al. |
| 9,651,922 B2 | 5/2017 | Hysek et al. |
| 9,659,482 B2 | 5/2017 | Yang et al. |
| 9,680,831 B2 | 6/2017 | Jooste et al. |
| 9,709,956 B1 | 7/2017 | Ely et al. |
| 9,753,436 B2 | 9/2017 | Ely et al. |
| D800,172 S | 10/2017 | Akana |
| 9,800,717 B2 | 10/2017 | Ma et al. |
| 9,836,025 B2 | 12/2017 | Ely et al. |
| 9,873,711 B2 | 1/2018 | Hoover et al. |
| 9,874,945 B2 | 1/2018 | Fukumoto |
| 9,886,006 B2 | 2/2018 | Ely et al. |
| 9,891,590 B2 | 2/2018 | Shim et al. |
| 9,891,651 B2 | 2/2018 | Jackson et al. |
| 9,891,667 B2 | 2/2018 | Jung et al. |
| 9,898,032 B2 | 2/2018 | Hafez et al. |
| 9,913,591 B2 | 3/2018 | Lapetina et al. |
| 9,921,548 B2 | 3/2018 | Mitani |
| 9,927,902 B2 | 3/2018 | Burr et al. |
| 9,939,923 B2 | 4/2018 | Sharma |
| 9,946,297 B2 | 4/2018 | Nazzaro et al. |
| 9,952,558 B2 | 4/2018 | Ely |
| 9,952,682 B2 | 4/2018 | Zhang et al. |
| 9,971,305 B2 | 5/2018 | Ely et al. |
| 9,971,405 B2 | 5/2018 | Holenarsipur et al. |
| 9,971,407 B2 | 5/2018 | Holenarsipur et al. |
| 9,979,426 B2 | 5/2018 | Na et al. |
| 10,001,817 B2 | 6/2018 | Zambetti et al. |
| 10,012,550 B2 | 7/2018 | Yang |
| 10,018,966 B2 | 7/2018 | Ely et al. |
| 10,019,097 B2 | 7/2018 | Ely et al. |
| 10,037,006 B2 | 7/2018 | Ely |
| 10,037,081 B2 | 7/2018 | Grant |
| 10,048,802 B2 | 8/2018 | Shedletsky |
| 10,057,470 B2 | 8/2018 | Kim et al. |
| 10,061,399 B2 | 8/2018 | Bushnell et al. |
| 10,066,970 B2 | 9/2018 | Gowreesunker et al. |
| 10,092,203 B2 | 10/2018 | Mirov |
| 10,108,016 B2 | 10/2018 | Bosveld |
| 10,114,342 B2 | 10/2018 | Kim et al. |
| 10,145,711 B2 | 12/2018 | Boonsom et al. |
| 10,175,652 B2 | 1/2019 | Ely et al. |
| 10,190,891 B1 | 1/2019 | Rothkopf et al. |
| 10,203,662 B1 | 2/2019 | Lin et al. |
| 10,209,148 B2 | 2/2019 | Lyon et al. |
| 10,216,147 B2 | 2/2019 | Ely et al. |
| 10,222,755 B2 | 3/2019 | Coakley et al. |
| 10,222,756 B2 | 3/2019 | Ely et al. |
| 10,222,909 B2 | 3/2019 | Shedletsky et al. |
| 10,234,828 B2 | 3/2019 | Ely et al. |
| 10,241,593 B2 | 3/2019 | Chen |
| 10,296,125 B2 | 5/2019 | Ely et al. |
| 10,331,081 B2 | 6/2019 | Ely et al. |
| 10,331,082 B2 | 6/2019 | Ely et al. |
| 10,332,111 B2 | 6/2019 | Mokhasi et al. |
| 10,353,487 B2 | 7/2019 | Chung et al. |
| 10,379,629 B2 | 8/2019 | Bushnell et al. |
| 10,386,940 B2 | 8/2019 | Kim |
| 10,401,961 B2 | 9/2019 | Cruz-Hernandez et al. |
| 10,429,959 B2 | 10/2019 | Battlogg |
| 10,474,194 B1 | 11/2019 | Ell et al. |
| 10,503,258 B2 | 12/2019 | Holenarsipur et al. |
| 10,509,486 B2 | 12/2019 | Bushnell et al. |
| 10,524,671 B2 | 1/2020 | Lamego |
| 10,534,320 B2 | 1/2020 | Ferri et al. |
| 10,534,900 B2 | 1/2020 | Cheong et al. |
| 10,551,798 B1 | 2/2020 | Bushnell et al. |
| 10,572,053 B2 | 2/2020 | Ely et al. |
| 10,579,090 B2 | 3/2020 | Jackson et al. |
| 10,599,101 B2 | 3/2020 | Rothkopf et al. |
| 10,610,157 B2 | 4/2020 | Pandya et al. |
| 10,613,685 B2 | 4/2020 | Shedletsky |
| 10,627,783 B2 | 4/2020 | Rothkopf et al. |
| 10,655,988 B2 | 5/2020 | Boonsom et al. |
| 10,664,074 B2 | 5/2020 | Moussette et al. |
| 10,732,571 B2 | 8/2020 | Ely et al. |
| 10,765,019 B2 | 9/2020 | Werner |
| 10,845,764 B2 | 11/2020 | Ely et al. |
| 10,852,700 B2 | 12/2020 | Abramov |
| 10,852,855 B2 | 12/2020 | Niu |
| 10,871,385 B2 | 12/2020 | Kok |
| 10,884,549 B2 | 1/2021 | Shedletsky et al. |
| 10,936,071 B2 | 3/2021 | Pandya et al. |
| 10,942,491 B2 | 3/2021 | Rothkopf |
| 10,948,880 B2 | 3/2021 | Ely et al. |
| 10,955,937 B2 | 3/2021 | Bushnell et al. |
| 10,962,930 B2 | 3/2021 | Ely et al. |
| 10,962,935 B1 | 3/2021 | Ely et al. |
| 10,987,054 B2 | 4/2021 | Pandya et al. |
| 11,000,193 B2 | 5/2021 | Tal et al. |
| 11,002,572 B2 | 5/2021 | Boonsom et al. |
| 11,029,831 B2 | 6/2021 | Block et al. |
| 11,036,318 B2 | 6/2021 | Bokma et al. |
| 11,148,292 B2 | 10/2021 | Bryner et al. |
| 11,181,863 B2 | 11/2021 | Ely et al. |
| 11,194,298 B2 | 12/2021 | Roach et al. |
| 11,194,299 B1 * | 12/2021 | Taylor .................... G06F 3/016 |
| 11,221,590 B2 | 1/2022 | Rothkopf et al. |
| 11,347,189 B1 * | 5/2022 | Herrera ................. H04N 23/51 |
| 11,347,351 B2 | 6/2022 | Shedletsky et al. |
| 11,360,440 B2 | 6/2022 | Perkins et al. |
| 11,385,599 B2 | 7/2022 | Ely et al. |
| 11,474,483 B2 | 10/2022 | Rothkopf |
| 11,567,457 B2 | 1/2023 | Rothkopf et al. |
| 2002/0101457 A1 | 8/2002 | Lang |
| 2003/0174590 A1 | 9/2003 | Arikawa et al. |
| 2004/0047244 A1 | 3/2004 | Lino et al. |
| 2004/0082414 A1 | 4/2004 | Knox |
| 2004/0130971 A1 | 7/2004 | Ecoffet et al. |
| 2004/0264301 A1 | 12/2004 | Howard et al. |
| 2005/0075558 A1 | 4/2005 | Vecerina et al. |
| 2005/0088417 A1 | 4/2005 | Mulligan |
| 2006/0250377 A1 | 11/2006 | Zadesky et al. |
| 2007/0013775 A1 | 1/2007 | Shin |
| 2007/0050054 A1 | 3/2007 | Sambandam Guruparan et al. |
| 2007/0182708 A1 | 8/2007 | Poupyrev et al. |
| 2007/0211042 A1 | 9/2007 | Kim et al. |
| 2007/0222756 A1 | 9/2007 | Wu et al. |
| 2007/0229671 A1 | 10/2007 | Takeshita et al. |
| 2007/0247421 A1 | 10/2007 | Orsley et al. |
| 2008/0130914 A1 | 6/2008 | Cho |
| 2009/0051649 A1 | 2/2009 | Rondel |
| 2009/0073119 A1 | 3/2009 | Le et al. |
| 2009/0122656 A1 | 5/2009 | Bonnet et al. |
| 2009/0146975 A1 | 6/2009 | Chang |
| 2009/0152452 A1 | 6/2009 | Lee et al. |
| 2009/0217207 A1 | 8/2009 | Kagermeier et al. |
| 2009/0285443 A1 | 11/2009 | Camp et al. |
| 2009/0312051 A1 | 12/2009 | Hansson et al. |
| 2009/0312655 A1 | 12/2009 | Lo |
| 2010/0033430 A1 | 2/2010 | Kakutani et al. |
| 2010/0053468 A1 | 3/2010 | Havrill |
| 2010/0081375 A1 | 4/2010 | Rosenblatt et al. |
| 2010/0149099 A1 | 6/2010 | Elias |
| 2011/0007468 A1 | 1/2011 | Burton et al. |
| 2011/0090148 A1 | 4/2011 | Li et al. |
| 2011/0158057 A1 | 6/2011 | Brewer et al. |
| 2011/0242064 A1 | 10/2011 | Ono et al. |
| 2011/0270358 A1 | 11/2011 | Davis et al. |

(56) References Cited

U.S. PATENT DOCUMENTS

| | | |
|---|---|---|
| 2012/0067711 A1 | 3/2012 | Yang |
| 2012/0068857 A1 | 3/2012 | Rothkopf et al. |
| 2012/0075082 A1 | 3/2012 | Rothkopf et al. |
| 2012/0112859 A1 | 5/2012 | Park et al. |
| 2012/0113044 A1 | 5/2012 | Strazisar et al. |
| 2012/0206248 A1 | 8/2012 | Biggs |
| 2012/0272784 A1 | 11/2012 | Bailey et al. |
| 2013/0037396 A1 | 2/2013 | Yu |
| 2013/0087443 A1 | 4/2013 | Kikuchi |
| 2013/0191220 A1 | 7/2013 | Dent et al. |
| 2013/0235704 A1 | 9/2013 | Grinberg |
| 2013/0261405 A1 | 10/2013 | Lee et al. |
| 2013/0335196 A1 | 12/2013 | Zhang et al. |
| 2014/0009397 A1 | 1/2014 | Gillespie |
| 2014/0045547 A1 | 2/2014 | Singamsetty et al. |
| 2014/0071098 A1 | 3/2014 | You |
| 2014/0073486 A1 | 3/2014 | Ahmed et al. |
| 2014/0132516 A1 | 5/2014 | Tsai et al. |
| 2014/0197936 A1 | 7/2014 | Biggs et al. |
| 2014/0340318 A1 | 11/2014 | Stringer et al. |
| 2014/0347289 A1 | 11/2014 | Suh et al. |
| 2014/0368442 A1 | 12/2014 | Vahtola |
| 2014/0375579 A1 | 12/2014 | Fujiwara |
| 2015/0049059 A1 | 2/2015 | Zadesky et al. |
| 2015/0098309 A1 | 4/2015 | Adams et al. |
| 2015/0124415 A1 | 5/2015 | Goyal et al. |
| 2015/0186609 A1 | 7/2015 | Utter, II |
| 2015/0221460 A1 | 8/2015 | Teplitxky et al. |
| 2015/0293592 A1 | 10/2015 | Cheong |
| 2015/0320346 A1 | 11/2015 | Chen |
| 2015/0338642 A1 | 11/2015 | Sanford |
| 2015/0366098 A1 | 12/2015 | Lapetina et al. |
| 2016/0018846 A1 | 1/2016 | Zenoff |
| 2016/0054813 A1 | 2/2016 | Shediwy et al. |
| 2016/0062623 A1 | 3/2016 | Howard et al. |
| 2016/0069713 A1 | 3/2016 | Ruh et al. |
| 2016/0147432 A1 | 5/2016 | Shi et al. |
| 2016/0170598 A1 | 6/2016 | Zambetti et al. |
| 2016/0170608 A1 | 6/2016 | Zambetti et al. |
| 2016/0170624 A1 | 6/2016 | Zambetti et al. |
| 2016/0241688 A1 | 8/2016 | Vossoughi |
| 2016/0253487 A1 | 9/2016 | Sarkar et al. |
| 2016/0306446 A1 | 10/2016 | Chung et al. |
| 2016/0320583 A1 | 11/2016 | Hall, Jr. |
| 2016/0327911 A1 | 11/2016 | Eim et al. |
| 2016/0338642 A1 | 11/2016 | Parara et al. |
| 2016/0378069 A1 | 12/2016 | Rothkopf et al. |
| 2016/0378070 A1 | 12/2016 | Rothkopf et al. |
| 2017/0027461 A1 | 2/2017 | Shin et al. |
| 2017/0031449 A1 | 2/2017 | Karsten et al. |
| 2017/0061863 A1 | 3/2017 | Eguchi |
| 2017/0069443 A1 | 3/2017 | Wang et al. |
| 2017/0069444 A1 | 3/2017 | Wang et al. |
| 2017/0069447 A1 | 3/2017 | Wang et al. |
| 2017/0216519 A1 | 8/2017 | Vouillamoz |
| 2017/0216668 A1 | 8/2017 | Burton et al. |
| 2017/0238138 A1 | 8/2017 | Aminzade |
| 2017/0251561 A1 | 8/2017 | Fleck et al. |
| 2017/0269715 A1 | 9/2017 | Kim et al. |
| 2017/0285404 A1 | 10/2017 | Kubota et al. |
| 2017/0301314 A1 | 10/2017 | Kim et al. |
| 2017/0307414 A1 | 10/2017 | Ferri et al. |
| 2017/0331869 A1 | 11/2017 | Bendahan et al. |
| 2017/0357465 A1 | 12/2017 | Dzeryn et al. |
| 2018/0059624 A1 | 3/2018 | James |
| 2018/0196517 A1 | 7/2018 | Tan et al. |
| 2018/0225701 A1 | 8/2018 | Han |
| 2018/0235491 A1 | 8/2018 | Bayley et al. |
| 2018/0337551 A1 | 11/2018 | Park |
| 2019/0025940 A1 | 1/2019 | Shim et al. |
| 2019/0056700 A1 | 2/2019 | Matsuno |
| 2019/0072911 A1 | 3/2019 | Ely et al. |
| 2019/0072912 A1 | 3/2019 | Pandya et al. |
| 2019/0088583 A1 | 3/2019 | Ashikaga et al. |
| 2019/0278232 A1 | 9/2019 | Ely et al. |
| 2019/0317454 A1 | 10/2019 | Holenarsipur et al. |
| 2020/0041962 A1 | 2/2020 | Beyhs |
| 2020/0064779 A1 | 2/2020 | Pandya et al. |
| 2020/0073339 A1* | 3/2020 | Roach ............... G04G 17/08 |
| 2020/0159172 A1 | 5/2020 | Bushnell et al. |
| 2020/0310609 A1 | 10/2020 | Ham |
| 2021/0055696 A1 | 2/2021 | Ely |
| 2021/0181682 A1 | 6/2021 | Ely et al. |
| 2021/0181691 A1 | 6/2021 | Rothkopf et al. |
| 2021/0181692 A1 | 6/2021 | Rothkopf et al. |
| 2021/0181865 A1 | 6/2021 | Bushnell et al. |
| 2021/0255590 A1 | 8/2021 | Ely et al. |
| 2021/0303081 A1* | 9/2021 | Kuboyama ............ G04C 3/001 |
| 2021/0353226 A1* | 11/2021 | Hiemstra ............. A61B 5/7435 |
| 2021/0373501 A1 | 12/2021 | Pandya et al. |
| 2021/0405594 A1* | 12/2021 | Holenarsipur ......... G04G 21/08 |
| 2022/0043397 A1* | 2/2022 | Ely ..................... G04G 21/025 |
| 2022/0043402 A1* | 2/2022 | Roach ................. G04G 21/025 |
| 2022/0075328 A1 | 3/2022 | Taylor |
| 2022/0299944 A1 | 9/2022 | Ely et al. |
| 2022/0326660 A1 | 10/2022 | Perkins et al. |
| 2023/0012897 A1 | 1/2023 | Bushnell et al. |
| 2023/0013283 A1 | 1/2023 | Herrera et al. |
| 2023/0028554 A1 | 1/2023 | Rothkopf et al. |
| 2023/0097827 A1 | 3/2023 | Rothkopf et al. |
| 2023/0101015 A1 | 3/2023 | Ely et al. |
| 2023/0161299 A1 | 5/2023 | Beyhs |

FOREIGN PATENT DOCUMENTS

| | | |
|---|---|---|
| CN | 1445627 | 10/2003 |
| CN | 1504843 | 6/2004 |
| CN | 1601408 | 3/2005 |
| CN | 1624427 | 6/2005 |
| CN | 1792295 | 6/2006 |
| CN | 1825224 | 8/2006 |
| CN | 101035148 | 9/2007 |
| CN | 101201587 | 6/2008 |
| CN | 201081979 | 7/2008 |
| CN | 101404928 | 4/2009 |
| CN | 201262741 | 6/2009 |
| CN | 101750958 | 6/2010 |
| CN | 201638168 | 11/2010 |
| CN | 101923314 | 12/2010 |
| CN | 102067070 | 5/2011 |
| CN | 102216959 | 10/2011 |
| CN | 202008579 | 10/2011 |
| CN | 102590925 | 7/2012 |
| CN | 102741772 | 10/2012 |
| CN | 102890443 | 1/2013 |
| CN | 202710937 | 1/2013 |
| CN | 103177891 | 6/2013 |
| CN | 103191557 | 7/2013 |
| CN | 103253067 | 8/2013 |
| CN | 103645804 | 3/2014 |
| CN | 203564224 | 4/2014 |
| CN | 103852090 | 6/2014 |
| CN | 203630524 | 6/2014 |
| CN | 103919536 | 7/2014 |
| CN | 103956006 | 7/2014 |
| CN | 203693601 | 7/2014 |
| CN | 203705837 | 7/2014 |
| CN | 203732900 | 7/2014 |
| CN | 103995456 | 8/2014 |
| CN | 104020660 | 9/2014 |
| CN | 203941395 | 11/2014 |
| CN | 104777987 | 4/2015 |
| CN | 104685794 | 6/2015 |
| CN | 204479929 | 7/2015 |
| CN | 204496177 | 7/2015 |
| CN | 104880937 | 9/2015 |
| CN | 104898406 | 9/2015 |
| CN | 204650147 | 9/2015 |
| CN | 105022947 | 11/2015 |
| CN | 105096979 | 11/2015 |
| CN | 105339871 | 2/2016 |
| CN | 105547146 | 5/2016 |
| CN | 105556433 | 5/2016 |
| CN | 105683876 | 6/2016 |

(56) References Cited

FOREIGN PATENT DOCUMENTS

| | | |
|---|---|---|
| CN | 105760067 | 7/2016 |
| CN | 105955519 | 9/2016 |
| CN | 205645648 | 10/2016 |
| CN | 205721636 | 11/2016 |
| CN | 205750744 | 11/2016 |
| CN | 106236051 | 12/2016 |
| CN | 106557218 | 4/2017 |
| CN | 206147524 | 5/2017 |
| CN | 206209589 | 5/2017 |
| CN | 107111342 | 8/2017 |
| CN | 107122088 | 9/2017 |
| CN | 107966895 | 4/2018 |
| CN | 209560397 | 10/2019 |
| CN | 209625187 | 11/2019 |
| CN | 114220694 | 3/2022 |
| CN | 106125968 | 11/2022 |
| DE | 3706194 | 9/1988 |
| DE | 102008023651 | 11/2009 |
| DE | 102016215087 | 3/2017 |
| EP | 0165548 | 12/1985 |
| EP | 0556155 | 8/1993 |
| EP | 1345095 | 9/2003 |
| EP | 1519452 | 3/2005 |
| EP | 1669724 | 6/2006 |
| EP | 1832969 | 9/2007 |
| EP | 2375295 | 10/2011 |
| EP | 2579186 | 4/2013 |
| EP | 2720129 | 4/2014 |
| EP | 2884239 | 6/2015 |
| FR | 2030093 | 10/1970 |
| FR | 2801402 | 5/2001 |
| GB | 2433211 | 6/2007 |
| JP | S52151058 | 12/1977 |
| JP | S52164551 | 12/1977 |
| JP | S53093067 | 8/1978 |
| JP | S54087779 | 6/1979 |
| JP | S5708582 | 1/1982 |
| JP | S5734457 | 2/1982 |
| JP | S60103936 | 6/1985 |
| JP | S60103937 | 6/1985 |
| JP | H02285214 | 11/1990 |
| JP | H04093719 | 3/1992 |
| JP | H04157319 | 5/1992 |
| JP | H05203465 | 8/1993 |
| JP | H05312595 | 11/1993 |
| JP | H06050927 | 12/1994 |
| JP | H06331761 | 12/1994 |
| JP | H06347293 | 12/1994 |
| JP | H07116141 | 5/1995 |
| JP | H0914941 | 1/1997 |
| JP | H10161811 | 6/1998 |
| JP | H11121210 | 4/1999 |
| JP | H11191508 | 7/1999 |
| JP | 2000258559 | 9/2000 |
| JP | 2000316824 | 11/2000 |
| JP | 2000337892 | 12/2000 |
| JP | 2001084934 | 3/2001 |
| JP | 2001167651 | 6/2001 |
| JP | 2001202178 | 7/2001 |
| JP | 2001215288 | 8/2001 |
| JP | 2001524206 | 11/2001 |
| JP | 2002071480 | 3/2002 |
| JP | 2002165768 | 6/2002 |
| JP | 2003050668 | 2/2003 |
| JP | 2003151410 | 5/2003 |
| JP | 2003331693 | 11/2003 |
| JP | 2004184396 | 7/2004 |
| JP | 2004028979 | 11/2004 |
| JP | 2005017011 | 1/2005 |
| JP | 2005063200 | 3/2005 |
| JP | 2005099023 | 4/2005 |
| JP | 2005108630 | 4/2005 |
| JP | 2006101505 | 4/2006 |
| JP | 2006164275 | 6/2006 |
| JP | 3852854 | 12/2006 |
| JP | 2007101380 | 4/2007 |
| JP | 2007149620 | 6/2007 |
| JP | 2007248176 | 9/2007 |
| JP | 2007311153 | 11/2007 |
| JP | 2008053980 | 3/2008 |
| JP | 2008122124 | 5/2008 |
| JP | 2008122377 | 5/2008 |
| JP | 2008170436 | 7/2008 |
| JP | 2008235226 | 10/2008 |
| JP | 2009009382 | 1/2009 |
| JP | 2009070657 | 4/2009 |
| JP | 2009519737 | 5/2009 |
| JP | 2009540399 | 11/2009 |
| JP | 2010032545 | 2/2010 |
| JP | 2010515153 | 5/2010 |
| JP | 2010165001 | 7/2010 |
| JP | 2010186572 | 8/2010 |
| JP | 2010243344 | 10/2010 |
| JP | 2010244797 | 10/2010 |
| JP | 2011021929 | 2/2011 |
| JP | 2011165468 | 8/2011 |
| JP | 2011221659 | 11/2011 |
| JP | 2012053801 | 3/2012 |
| JP | 2013057516 | 3/2013 |
| JP | 2013079961 | 5/2013 |
| JP | 2013524189 | 6/2013 |
| JP | 3190075 | 4/2014 |
| JP | 5477393 | 4/2014 |
| JP | 2014512556 | 5/2014 |
| JP | 2014112222 | 6/2014 |
| JP | 2014174031 | 9/2014 |
| JP | 2017219448 | 12/2017 |
| JP | 2018510451 | 4/2018 |
| KR | 20010030477 | 4/2001 |
| KR | 200278568 | 3/2002 |
| KR | 20070011685 | 1/2007 |
| KR | 20070014247 | 2/2007 |
| KR | 100754674 | 9/2007 |
| KR | 20080028935 | 4/2008 |
| KR | 20080045397 | 5/2008 |
| KR | 2020100007563 | 7/2010 |
| KR | 20110011393 | 2/2011 |
| KR | 20110012784 | 2/2011 |
| KR | 20110103761 | 9/2011 |
| KR | 20110113368 | 10/2011 |
| KR | 20130036038 | 4/2013 |
| KR | 20130131873 | 12/2013 |
| KR | 20140051391 | 4/2014 |
| KR | 20140064689 | 5/2014 |
| KR | 20140104388 | 8/2014 |
| KR | 20160017070 | 2/2016 |
| KR | 20160048967 | 5/2016 |
| KR | 20170106395 | 9/2017 |
| NL | 1040225 | 11/2014 |
| RO | 129033 | 11/2013 |
| TW | 200633681 | 10/2006 |
| WO | WO2001/022038 | 3/2001 |
| WO | WO2001/069567 | 9/2001 |
| WO | WO2003/032538 | 4/2003 |
| WO | WO2010/058376 | 5/2010 |
| WO | WO2012/083380 | 6/2012 |
| WO | WO2012/094805 | 7/2012 |
| WO | WO2014/018118 | 1/2014 |
| WO | WO2014/200766 | 12/2014 |
| WO | WO2015/147756 | 10/2015 |
| WO | WO2016080669 | 5/2016 |
| WO | WO2016/104922 | 6/2016 |
| WO | WO2016/155761 | 10/2016 |
| WO | WO2016196171 | 12/2016 |
| WO | WO2016208835 | 12/2016 |
| WO | WO2017/013278 | 1/2017 |
| WO | WO2020 173085 | 9/2020 |

OTHER PUBLICATIONS

Author Unknown, "Fossil Q ups smartwatch game with handsome design and build," Business Mirror, Makati City, Philippines, 3 pages, Dec. 20, 2016.

(56) References Cited

OTHER PUBLICATIONS

Author Unknown, "How Vesag Helps Kids Women and Visitors," http://www.sooperarticles.com/health-fitness-articles/children-health-articles/how-vesag-helps-kids-women-visitors-218542.html, 2 pages, at least as early as May 20, 2015.
Author Unknown, "mHealth," http://mhealth.vesag.com/?m=201012, 7 pages, Dec. 23, 2010.
Author Unknown, "mHealth Summit 2010," http://www.virtualpressoffice.com/eventsSubmenu.do?page=exhibitorPage&showId=1551&companyId=5394, 5 pages, Nov. 18, 2010.
Author Unknown, "MyKronoz ZeTime: World's Most Funded Hybrid Smartwatch Raised over $3M on Kickstarter, Running until Apr. 27," Business Wire, New York, New York, 3 pages, Apr. 21, 2017.
Author Unknown, "RedEye mini Plug-in Universal Remote Adapter for iPhone, iPod touch and iPad," Amazon.com, 4 pages, date unknown.
Author Unknown, "Re iPhone Universal Remote Control—Infrared Remote Control Accessory for iPhone and iPod touch," http://www.amazon.com/iPhone-Universal-Remote-Control-Accessory/dp/tech-data/B0038Z4 . . . , 2 pages, at least as early as Jul. 15, 2010.
Author Unknown, "Vesag Wrist Watch for Dementia Care from VYZIN," http://vyasa-kaaranam-ketkadey.blogspot.com/2011/03/vesag-wrist-watch-for-dementia-care.html, 2 pages, Mar. 31, 2011.
Author Unknown, "Vyzin Electronics Private Limited launches Vesag Watch," http://www.virtualpressoffice.com/showJointPage.do?page=jp&showId=1544, 5 pages, Jan. 6, 2011.
Author Unknown, "Vyzin Unveiled Personal Emergency Response System (PERS) with Remote Health Monitoring That Can Be Used for Entire Family," http://www.24-7pressrelease.com/press-release/vyzin-unveiled-personal-emergency-response-system-pers-with-remote-health-monitoring-that-can-be-used-for-entire-family-219317.php, 2 pages, Jun. 17, 2011.
Author Unknown, "DeskThorityNet, Optical Switch Keyboards," http://deskthority.net/keyboards-f2/optical-switch-keyboards-t1474.html, 22 pages, Jul. 11, 2015.
Epstein et al., "Economical, High-Performance Optical Encoders," Hewlett-Packard Journal, pp. 99-106, Oct. 1988. [text only version].
GreyB, "Google Watch: Convert your arm into a keyboard," http://www.whatafuture.com/2014/02/28/google-smartwatch/#sthash.Yk35cDXK.dpbs, 3 pages, Feb. 28, 2014.
IBM, "Additional Functionality Added to Cell Phone via "Learning" Function Button," www.ip.com, 2 pages, Feb. 21, 2007.
Kim, Joseph, "2010 mHealth Summit Emerges as Major One-Stop U.S. Venue for Mobile Health," http://www.medicineandtechnology.com/2010/08/2010-mhealth-summit-emerges-as-major.html, 3 pages, Aug. 26, 2010.
Krishnan et al., "A Miniature Surface Mount Reflective Optical Shaft Encoder," Hewlett-Packard Journal, Article 8, pp. 1-6, Dec. 1996.
Narayanaswami et al., "Challenges and considerations for the design and production of a purpose-optimized body-worn wristwatch computer," Defense, Security, and Cockpit Displays, 2004.
M.T. Raghunath et al., User Interfaces for Applications on a Wrist Watch, Personal and Ubiquitous Computing, vol. 6, No. 1, 2002, Springer.
Rick, "How VESAG Helps Health Conscious Citizens," http://sensetekgroup.com/2010/11/29/wireless-health-monitoring-system/, 2 pages, Nov. 29, 2010.
Sadhu, Rajendra, "How VESAG Helps People Who Want to 'Be There'?," http://ezinearticles.com/?How-Vesag-Helps-People-Who-Want-to-Be-There?&id=5423873, 1 page, Nov. 22, 2010.
Sherr, Sol, "Input Devices," p. 55, Mar. 1988.
Tran et al., "Universal Programmable Remote Control/Telephone," www.ip.com, 2 pages, May 1, 1992.
U.S. Appl. No. 17/377,482, filed Jul. 16, 2021, pending.
U.S. Appl. No. 17/840,222, filed Jun. 14, 2022, pending.
U.S. Appl. No. 17/899,498, filed Aug. 31, 2022, pending.
U.S. Appl. No. 17/951,020, filed Sep. 22, 2022, pending.

\* cited by examiner

SWITCH MODULE FOR ELECTRONIC CROWN ASSEMBLY

CROSS-REFERENCE TO RELATED APPLICATION(S)

This application is a continuation patent application of U.S. patent application Ser. No. 16/890,880, filed Jun. 2, 2020, and titled "Switch Module for Electronic Crown Assembly", the contents of which are incorporated herein by reference in its entirety.

FIELD

Embodiments generally relate to a switch module for an electronic device. More particularly, embodiments described herein relate to a switch module routing an external signal and a switch signal for an electronic device.

BACKGROUND

Electronic devices frequently use physical input devices to facilitate user interaction. For example, buttons, keys, dials, and the like can be physically manipulated by users to control operations of the device. Physical input devices may use various types of sensing mechanisms to translate the physical manipulation to signals usable by the electronic device. For example, buttons and keys may use collapsible dome switches to detect presses, while dials and other rotating input devices may use encoders or resolvers to detect rotational movements.

SUMMARY

Embodiments of the systems, devices, methods, and apparatuses described in the present disclosure are directed to a switch module for an electronic device.

One embodiment may take the form of an electronic watch that includes an enclosure, a processing unit, a display, and a crown assembly. The enclosure may define an interior volume and an opening into the interior volume. The processing unit may be positioned within the interior volume. The display may be operably coupled to the processing unit and configured to provide a graphical output. The crown assembly may be positioned at least partially within the interior volume, and may include an actuation member extending through the opening and defining a input surface for sensing an input signal along an exterior of the electronic watch. The crown assembly may further include a rotation sensor positioned within the interior volume and configured to detect a rotational input at the crown assembly. The crown assembly may further include a switch module positioned within the interior volume. The switch module may include a switch housing defining a recess, a persistent electrical contact positioned in the recess and conductively coupled to the processing unit, a switch electrical contact positioned in the recess and conductively coupled to the processing unit, and a conductive dome positioned at least partially in the recess and conductively coupled to the actuation member. The conductive dome may be configured to transition from an uncollapsed configuration to a collapsed configuration in response to a translational input at the actuation member. In the uncollapsed configuration and the collapsed configuration, the conductive dome may contact the persistent electrical contact to at least partially define a conductive path between the input surface and the processing unit. In the collapsed configuration, the conductive dome may contact the switch electrical contact to register the translational input. The graphical output may be responsive to the input signal, the rotational input, and the translational input.

Another embodiment may take the form of a switch module for a crown assembly for an electronic watch. The switch module may include a switch housing that includes a base defining a recess and a bracket for coupling the switch module to a device enclosure. The switch module may further include a conductive dome positioned at least partially in the recess and defining a first portion of a conductive path between an actuation member and a processing unit. The conductive dome may be configured to transition from an uncollapsed configuration to a collapsed configuration in response to a translational input at the actuation member. The switch module may further include a friction guard contacting the conductive dome and configured to be positioned between the conductive dome and the actuation member. The friction guard may define a second portion of the conductive path. The switch module may further include a persistent electrical contact positioned in the recess and contacting the conductive dome, the persistent electrical contact defining a third portion of the conductive path. The switch module may further include a first conductive member at least partially encapsulated within the base and defining a fourth portion of the conductive path. The switch module may further include a switch electrical contact positioned in the recess and configured to contact the conductive dome in the collapsed configuration to register the translational input. The switch module may further include a second conductive member at least partially encapsulated within the base and configured to conductively couple the switch electrical contact to the processing unit.

Another embodiment may take the form of an electronic watch that includes an enclosure, a processing unit, and a crown assembly. The enclosure may define an interior volume and an opening into the interior volume. The processing unit may be positioned within the interior volume. The crown assembly may be positioned at least partially within the interior volume, and may include an actuation member extending through the opening and defining a input surface for sensing an input signal along an exterior of the electronic watch. The crown assembly may further include a rotation sensor positioned within the interior volume and configured to detect a rotational input at the crown assembly. The crown assembly may further include a switch module positioned within the interior volume. The switch module may include a switch housing defining a recess, a conductive dome positioned in the recess and configured to collapse in response to a translational input at the crown assembly, and a friction guard at least partially defining a conductive path between the input surface and the processing unit. The friction guard may include a support member attached to the switch housing, a translating portion contacting the actuation member, and a first flexure and a second flexure extending from the support member and at least partially surrounding the translating portion, the first flexure and the second flexure configured to allow the translating portion to move relative to the switch housing.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1:
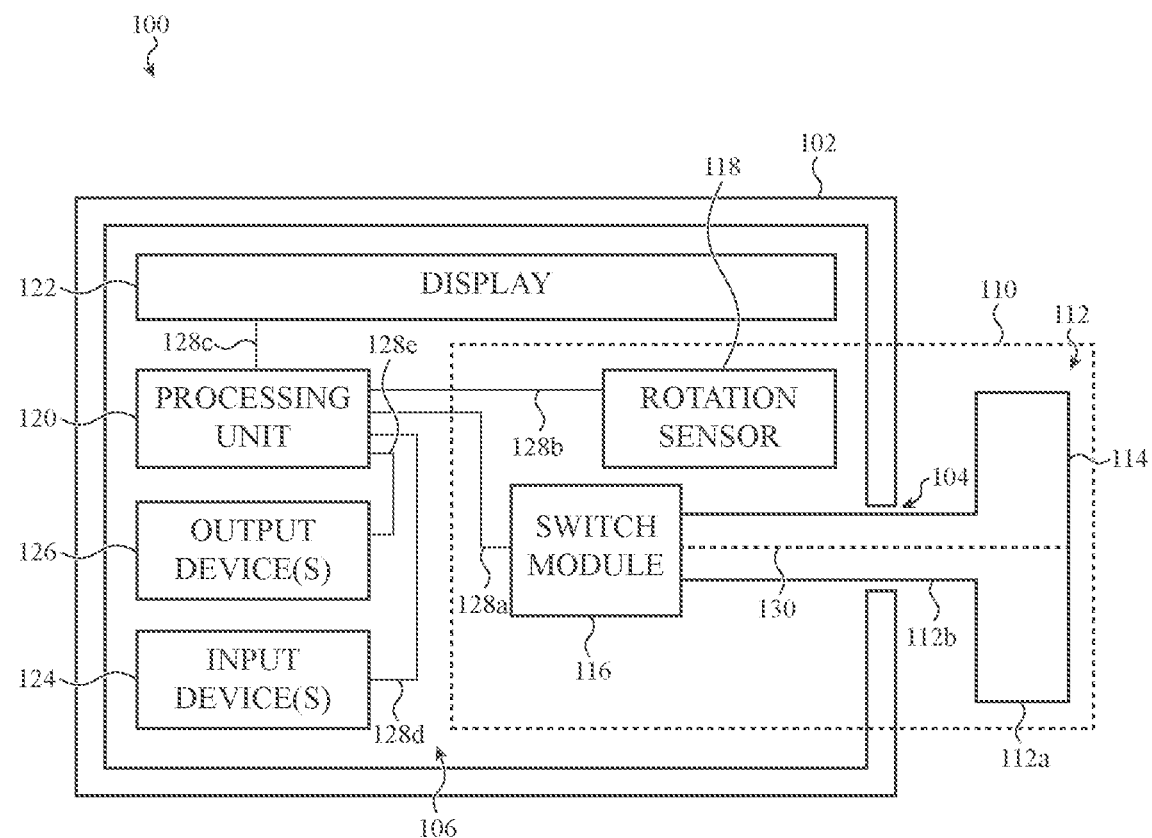
FIG. 1 is a functional block diagram of an electronic device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to electronic devices, and in particular to a switch module for a crown assembly that receives rotational inputs and translational inputs, and includes an actuation member defining an input surface for receiving sensor inputs, such as touch inputs, electrocardiogram (ECG) signals, and the like. The switch module may provide at least a portion of a conductive path from the input surface of the crown assembly to a processing unit or other circuitry of the electronic device. The conductive path may be electrically isolated from one or more additional components of the crown assembly and/or the electronic device, and may allow signals from to be transmitted between the input surface and the processing unit.

The switch module may include a conductive dome and a friction guard that is positioned between the conductive dome and the actuation member of the crown assembly. The conductive dome and/or the friction guard may define at least a portion of the conductive path from the input surface to the processing unit.

The conductive dome may collapse in response to a translational input moving the actuation member from an unactuated position to an actuated position. The conductive dome and/or the friction guard may provide an outward biasing force that maintains the actuation member in the unactuated position absent an inward force on the actuation member. The outward biasing force may be a spring force exerted by the conductive dome and/or the friction guard on the actuation member. A translational input may be provided to the crown assembly in the form of an inward force that overcomes the outward biasing force and causes the actuation member to translate inward to an actuated position. When the inward force is removed or reduced, the outward biasing force may cause the actuation member to return to the unactuated position.

When the actuation member is in the unactuated position, the conductive dome is in an uncollapsed configuration. When the actuation member is in the actuated position, the conductive dome is in a collapsed configuration. In the uncollapsed configuration and/or the collapsed configuration, the conductive dome may contact a first electrical contact that is conductively coupled to the processing unit, thereby facilitating transmission of signals between the input surface and the processing unit. In the collapsed configuration, the conductive dome may contact a second electrical contact, which may close a circuit to register the translational input. In the uncollapsed configuration and/or the collapsed configuration, the conductive dome may contact a reference electrical contact that provides a bias voltage for detecting translational inputs and/or input signals at the input surface. When the conductive dome contacts the second electrical contact, it may close a circuit that includes the reference electrical contact, which, in turn, may register a translational input.

The conductive dome may define one or more conductive routes that are electrically isolated from one another. The conductive dome may include vias or other structural elements for defining the isolated conductive routes. The conductive dome may define a first conductive path between a friction guard and the first electrode for transmitting signals between the sensor and the processing unit. The conductive dome may define a second conductive path between the second electrical contact and the reference electrical contact for detecting translational inputs. The first and second conductive paths may be electrically isolated from one another to prevent signal interference.

In embodiments in which the friction guard provides at least a portion of the outward biasing force, the friction guard may include a translating portion and one or more flexures that allow the translating portion to move. The friction guard may act as a spring, with the flexures exerting a reaction force on the translating portion (and therefore on the actuation member) that is dependent on the position of the translating portion. The spring dynamics of the friction guard may be defined by the material properties, the thickness, and the length of the flexures.

The switch module may include a switch housing that at least partially surrounds one or more components of the switch module. The housing may define a recess in which the conductive dome, the friction guard, and/or one or more of the electrical contacts are positioned. The switch housing may include a bracket or other fastening component for coupling the switch module to the enclosure or one or more other components of the electronic watch. In some cases, the electrical contacts may be at least partially encapsulated within the switch housing. As used herein, "encapsulated" may refer to a component that is contacted by and partially or completely surrounded by another component. For example, the electrical contacts may be encapsulated within a base of the switch housing by injection molding.

The term "attached," as used herein, may refer to two or more elements, structures, objects, components, parts or the like that are physically affixed, fastened, and/or retained to one another. The term "coupled," as used herein, may refer to two or more elements, structures, objects, components, parts or the like that are physically attached to one another, operate with one another, communicate with one another, are in electrical connection with one another, and/or otherwise interact with one another. Accordingly, while elements attached to one another are coupled to one another, the reverse is not required. As used herein, "operably coupled" or "electrically coupled" may refer to two or more devices that are coupled in any suitable manner for operation and/or communication, including wiredly, wirelessly, or some combination thereof. As used herein, "conductively coupled" may refer to two or more elements, structures, objects, components, parts or the like that are coupled in any suitable manner for facilitating the transmission of electrical current therebetween.

These and other embodiments are discussed with reference to FIGS. 1-7. However, those skilled in the art will readily appreciate that the detailed description given herein with respect to these figures is for explanatory purposes only and should not be construed as limiting.

FIG. 1 is a functional block diagram of an electronic device 100. In some examples, the device 100 may be an electronic watch or electronic health monitoring device. The electronic device 100 may include a device enclosure 102 that defines an interior volume 106 of the device. The device may include a crown assembly 110, a processing unit 120, a display 122, one or more input devices 124, and one or more output devices 126 positioned at least partially within the interior volume. Each of the components of the electronic device 100 may be operably coupled to the processing unit 120, for example via connectors 128a-e.

In some cases, the electronic device 100 includes a crown assembly 110 configured to receive translational inputs, rotational inputs, touch inputs and/or biometric signals. Inputs received at the crown assembly 110 may result in changes in outputs provided by the electronic device 100, such as a graphical output of the display 122, and/or otherwise modify operations of the electronic device. In some cases, the crown assembly 110 may be positioned along a side of the enclosure 102, and may extend through an opening 104 defined in the enclosure and into the interior volume 106.

The crown assembly 110 may include an actuation member 112 that may be translated (e.g., by a user) to provide translational inputs, rotated to provide rotational inputs, and touched to provide touch inputs and/or biometric signals. The crown assembly 110 may include a switch module 116 that is used to detect translational inputs to the crown assembly. The switch module 116 may also define at least a part of a conductive path between the actuation member 112 and the processing unit 120. This may facilitate the transmission of touch inputs and/or biometric signals from the actuation member 112 to the processing unit 120.

The actuation member 112 may include a crown body 112a positioned at least partially outside the enclosure 102 and a crown shaft 112b extending through the opening 104 and positioned at least partially within the enclosure 102. As shown, the crown body 112a and the crown shaft 112b may be formed as a unitary structure, though other actuation members may have different components and/or configurations, and may be defined by several different components that are attached together. The actuation member 112 may be formed from or include a conductive material (e.g., metal, carbon fiber, conductive polymer, conductive ceramics, or the like).

The actuation member 112 may define a input surface 114 that users can touch to provide touch inputs or biological signals to the electronic device 100. The actuation member 112 and the switch module 116 may form at least a portion of a conductive path 130 between the input surface 114 and the processing unit 120. This may facilitate the transmission of input signals from the input surface 114 to the processing unit 120. The input surface 114 may be an electrically conductive surface. The electrical conductivity of the input surface 114 may facilitate a conductive path (e.g., conductive path 130) from a user's finger in contact with the input surface to other components of the electronic device.

Additionally or alternatively, the crown assembly 110 may include one or more sensing elements for detecting touch inputs and/or biological signals. Example sensing elements include capacitive sensors, ultrasonic sensors, optical sensors, and the like. The actuation member 112 and/or the switch module 116 may define at least a portion of a conductive path between the sensing element(s) and the processing unit 120.

The input surface 114 may function as an electrode to sense input signals, which may include voltages or signals indicative of one or more touch inputs and/or biological parameters of a user in contact with the conductive surface. The enclosure 102 may define another touch-sensitive or conductive surface that is electrically coupled to the processing unit 120 and also functions as an electrode. The processing unit 120 may determine an electrocardiogram using outputs of the electrodes of the input surface 114 and the enclosure 102. In various embodiments, the crown assembly 110 is electrically isolated from the enclosure 102. This may prevent or mitigate signal interference between the electrodes, for example to allow separate measurements at each electrode.

The crown assembly 110 may include a rotation sensor 118 positioned within the interior volume 106 for detecting rotation of the actuation member 112. The rotation sensor 118 may include one or more light emitters and/or light detectors. The light emitter(s) may illuminate an encoder pattern or other rotating portion of the actuation member 112. The encoder pattern may be carried on (e.g., formed on, printed on, etc.) the crown shaft 112b or another component of the actuation member 112. The light detector(s) may receive light emitted by the light emitter(s) and reflected from the actuation member 112. The light detector(s) may be operably coupled to the processing unit 120, which may determine a direction of rotation, speed of rotation, angular position, translation, or other state(s) of the actuation member 112. In some embodiments, the rotation sensor 118 may detect rotation of the actuation member 112 by detecting rotation of the crown shaft 112b. The rotation sensor 118 may be electrically coupled to the processing unit 120 of the electronic device by a connector 128b.

As discussed above, the display 122 may be disposed at least partially within the enclosure 102. The display 122 provides a graphical output, for example associated with an operating system, user interface, and/or applications of the electronic device 100. In one embodiment, the display 122 includes one or more sensors and is configured as a touch-sensitive (e.g., single-touch, multi-touch) and/or force-sensitive display to receive inputs from a user. The display 122 is operably coupled to the processing unit 120 of the electronic device 100, for example by a connector 128c.

A graphical output of the display 122 may be responsive to inputs provided at the crown assembly 110, the display 122, and/or another input device 124. For example, the processing unit 120 may be configured to modify the graphical output of the display 122 in response to determining an electrocardiogram, receiving rotational inputs, receiving translational inputs, or receiving touch inputs. The display 122 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 122 is positioned beneath and viewable through a cover sheet that forms at least a portion of the enclosure 102.

Broadly, the input devices 124 may detect various types of input, and the output devices 126 may provide various types of output. The processing unit 120 may receive input signals from the input devices 124 in response to inputs detected by the input devices. The processing unit 120 may interpret input signals received from one or more of the input devices 124 and transmit output signals to one or more of the output devices 126. The output signals may cause the output devices 126 to provide one or more outputs. Detected input at one or more of the input devices 124 may be used to control one or more functions of the device 100. In some cases, one or more of the output devices 126 may be configured to provide outputs that are dependent on, or manipulated in response to, the input detected by one or more of the input devices 124. The outputs provided by one or more of the output devices 126 may also be responsive to, or initiated by, a program or application executed by the processing unit 120 and/or an associated companion device.

In various embodiments, the input devices 124 may include any suitable components for detecting inputs. Examples of input devices 124 include audio sensors (e.g., microphones), optical or visual sensors (e.g., cameras, visible light sensors, or invisible light sensors), proximity sensors, touch sensors, force sensors, mechanical devices (e.g., crown assemblies, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 124 may be configured to detect one or more particular types of input and provide a signal (e.g., an input signal) corresponding to the detected input. The signal may be provided, for example, to the processing unit 120.

In some cases, the input devices 124 include set of one or more electrodes. An electrode may be a conductive portion of the device 100 that contacts or is configured to be in contact with a user. The electrodes may be disposed on one or more exterior surfaces of the device 100, including a surface of the crown assembly 110, the enclosure 102, and the like. The processing unit 120 may monitor for voltages or signals received on at least one of the electrodes. In some embodiments, one of the electrodes may be permanently or switchably coupled to a device ground. The electrodes may be used to provide an electrocardiogram (ECG) function for the device 100. For example, a 2-lead ECG function may be provided when a user of the device 100 contacts first and second electrodes that receive signals from the user. As another example, a 3-lead ECG function may be provided when a user of the device 100 contacts first and second electrodes that receive signals from the user, and a third electrode that grounds the user to the device 100. In both the 2-lead and 3-lead ECG embodiments, the user may press the first electrode against a first part of their body and press the second electrode against a second part of their body. The third electrode may be pressed against the first or second body part, depending on where it is located on the device 100. In some cases, the enclosure 102 of the device 100 may function as an electrode. In some cases, input devices, such as buttons, crowns, and the like, may function as an electrode.

The output devices 126 may include any suitable components for providing outputs. Examples of output devices 126 include audio output devices (e.g., speakers), visual output devices (e.g., lights or displays), tactile output devices (e.g., haptic output devices), communication devices (e.g., wired or wireless communication devices), and so on, or some combination thereof. Each output device 126 may be configured to receive one or more signals (e.g., an output signal provided by the processing unit 120) and provide an output corresponding to the signal.

The processing unit 120 may be operably coupled to the input devices 124 and the output devices 126, for example by connectors 128d and 128e. The processing unit 120 may be adapted to exchange signals with the input devices 124 and the output devices 126. For example, the processing unit 120 may receive an input signal from an input device 124 that corresponds to an input detected by the input device. The processing unit 120 may interpret the received input signal to determine whether to provide and/or change one or more outputs in response to the input signal. The processing unit 120 may then send an output signal to one or more of the output devices 126, to provide and/or change outputs as appropriate. Example processing units are discussed below with respect to FIG. 7.

Figure 2A:
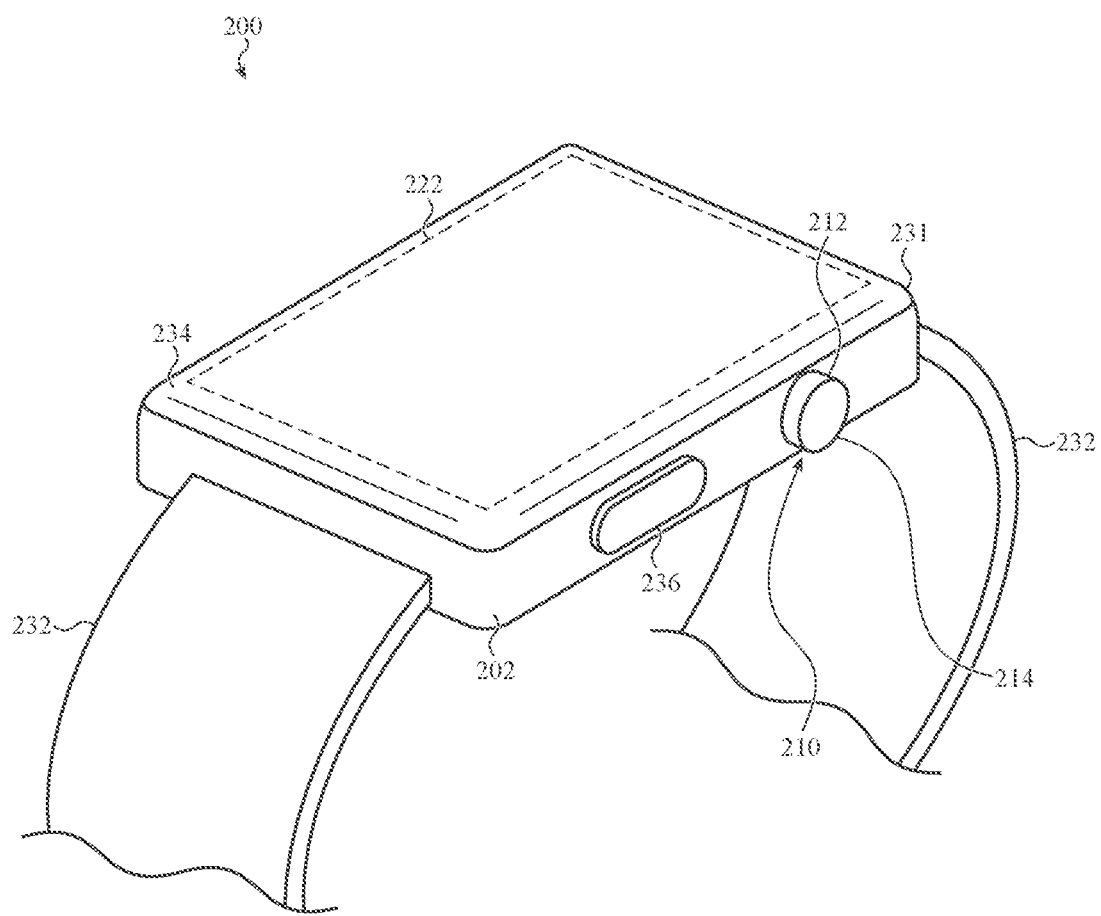
FIGS. 2A-2C show an example of a watch that incorporates a switch module as described herein.

FIG. 2A shows an example of a watch 200 (e.g., an electronic watch or smart watch) that incorporates a switch module as described herein. The watch 200 may include a watch body 231 and a watch band 232. Other devices that may incorporate a crown assembly include other wearable electronic devices, other timekeeping devices, other health monitoring or fitness devices, other portable computing devices, mobile phones (including smart phones), tablet computing devices, digital media players, or the like. The watch 200 may have similar components, structure, and/or functionality as the device 100 described with respect to FIG. 1.

The watch body 231 may include an enclosure 202. The enclosure 202 may include a front side enclosure member that faces away from a user's skin when the watch 200 is worn by a user, and a back side enclosure member that faces toward the user's skin. Alternatively, the enclosure 202 may include a singular enclosure member, or more than two enclosure members. The one or more enclosure members may be metallic, plastic, ceramic, glass, or other types of enclosure members (or combinations of such materials).

The enclosure 202 may include a cover sheet 234 mounted to a front side of the watch body 231 (i.e., facing away from a user's skin) and may protect a display 222 mounted within the enclosure 102. The display 222 may produce graphical output that may be viewable by a user through the cover sheet 234. In some cases, the cover sheet 234 may be part of a display stack, which display stack may include a touch sensing or force sensing capability. The display may be configured to depict a graphical output of the watch 200, and a user may interact with the graphical output (e.g., using a finger, stylus, or other pointer). As one example, the user may select (or otherwise interact with) a graphic, icon, or the like presented on the display by touching or pressing (e.g., providing touch input) on the cover sheet 234 at the location of the graphic. As used herein, the term "cover sheet" may be used to refer to any transparent, semi-transparent, or translucent surface made out of glass, a crystalline material (such as sapphire or zirconia), plastic, or the like. Thus, it should be appreciated that the term "cover sheet," as used herein, encompasses amorphous solids as well as crystalline solids. The cover sheet 234 may form a part of the enclosure 202. In some examples, the cover sheet 234 may be a sapphire cover sheet. The cover sheet 234 may also be formed of glass, plastic, or other materials.

In some embodiments, the watch body 231 may include an additional cover sheet (not shown) that forms a part of the enclosure 202. The additional cover sheet may have one or more electrodes thereon. For example, the watch body 231 may include an additional cover sheet mounted to a back side of the watch body 231 (i.e., facing toward a user's skin). The one or more electrodes on the additional cover sheet may be used to determine a biological parameter, such as a heart rate, an electrocardiogram, or the like. In some cases, the electrodes are used in combination with one or more additional electrodes, such as a surface of a crown assembly or other input device.

The watch body 231 may include at least one input device or selection device, such as a crown assembly, scroll wheel, knob, dial, button, or the like, which input device may be operated by a user of the watch 200. In some embodiments, the watch 200 includes a crown assembly 210 that includes an actuation member 212. The enclosure 202 may define an opening through which the actuation member 212 extends. The actuation member 212 may be accessible to a user exterior to the enclosure 202. The actuation member 212 may be user-rotatable, and may be manipulated (e.g., rotated, pressed) by a user. The actuation member 212 may be mechanically, electrically, magnetically, and/or optically coupled to components within the enclosure 202, as one example. A user's manipulation of the actuation member 212 may be used, in turn, to manipulate or select various elements displayed on the display, to adjust a volume of a speaker, to turn the watch 200 on or off, and so on.

The enclosure 202 may also include an opening through which a button 236 protrudes. The button 236 may be used to provide inputs to the watch 200. In some embodiments, the actuation member 212, scroll wheel, knob, dial, button 236, or the like may be touch sensitive, conductive, and/or have a conductive surface, and a signal route may be provided between the conductive portion of the actuation member 212, scroll wheel, knob, dial, button 236, or the like and a circuit within the watch body 231, such as a processing unit.

The enclosure 202 may include structures for attaching the watch band 232 to the watch body 231. In some cases, the structures may include elongate recesses or openings through which ends of the watch band 232 may be inserted and attached to the watch body 231. In other cases (not shown), the structures may include indents (e.g., dimples or depressions) in the enclosure 202, which indents may receive ends of spring pins that are attached to or threaded through ends of a watch band to attach the watch band to the watch body. The watch band 232 may be used to secure the watch 200 to a user, another device, a retaining mechanism, and so on.

In some examples, the watch 200 may lack any or all of the cover sheet 234, the display 222, the crown assembly 210, or the button 236. For example, the watch 200 may include an audio input or output interface, a touch input interface, a force input or haptic output interface, or other input or output interface that does not require the display, crown assembly 210, or button 236. The watch 200 may also include the aforementioned input or output interfaces in addition to the display 222, crown assembly 210, or button 236. When the watch 200 lacks the display, the front side of the watch 200 may be covered by the cover sheet 234, or by a metallic or other type of enclosure member.

Figure 2B:
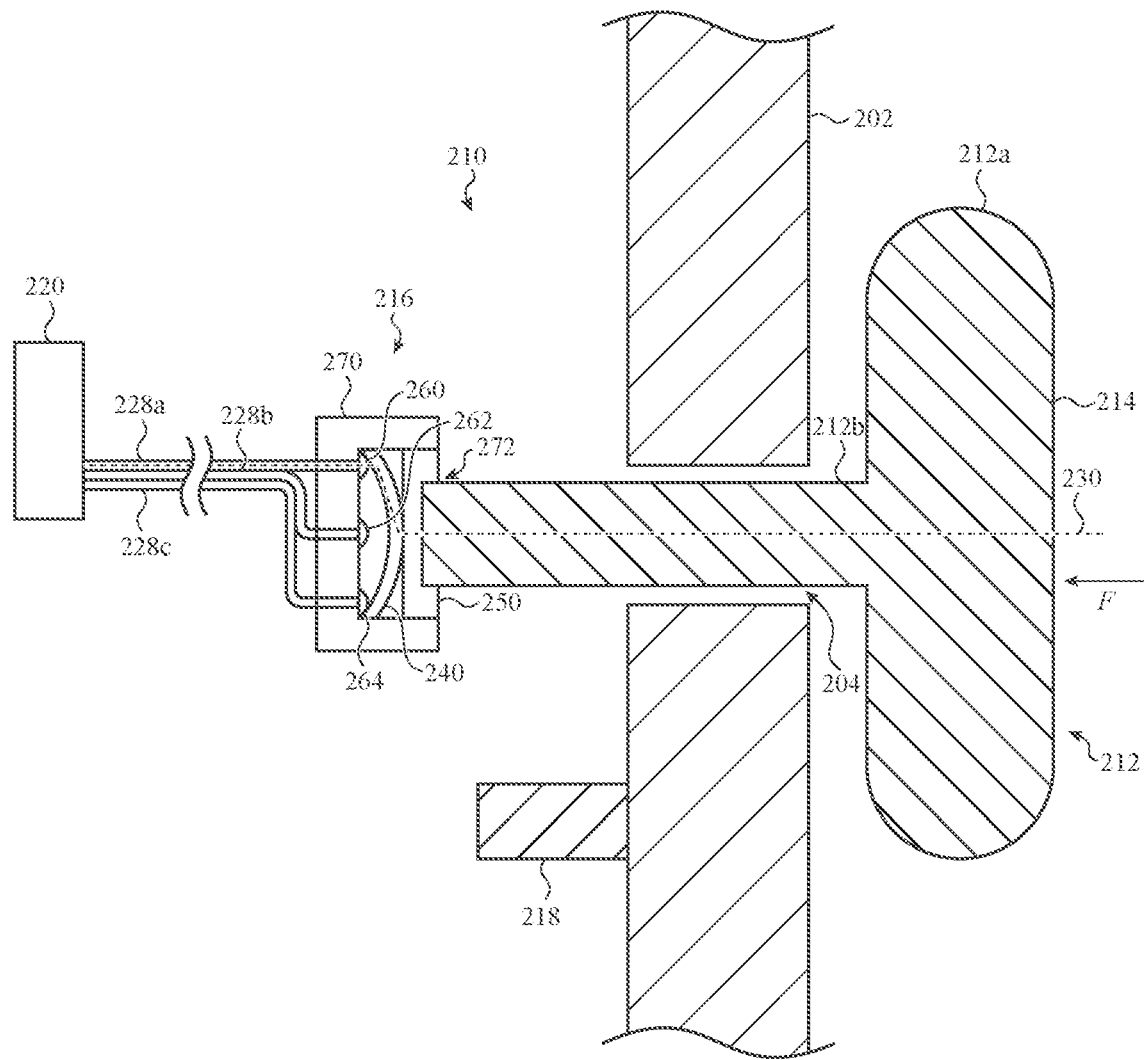

FIG. 2B depicts a partial cross-sectional view of the example watch 200, taken through section line A-A of FIG. 2A. The crown assembly 210 may extend through an opening 204 in the enclosure 202. The actuation member 212 may include a crown body 212a positioned at least partially outside the enclosure 202 and a crown shaft 212b extending through the opening 204 and positioned at least partially within the enclosure 202. As shown, the crown body 212a and the crown shaft 212b may be formed as a unitary structure, though other actuation members may have different components and/or configurations, and may be defined by several different components that are attached together. The actuation member 212 may be formed from or include a conductive material (e.g., metal, carbon fiber, conductive polymer, conductive ceramics, or the like).

The crown assembly 210 may include a switch module 216 that is used to detect translational inputs to the crown assembly. The actuation member 212 may define a input surface 214 that users can touch to provide touch inputs or biological signals to the watch 200. The actuation member 212 and the switch module 216 may form at least a portion of a conductive path 230 between the input surface 214 and the processing unit 220. This may facilitate the transmission of inputs and/or signals from the input surface 214 to the processing unit 220. The input surface 214 may be an electrically conductive surface. The electrical conductivity of the input surface 214 may facilitate a conductive path (e.g., conductive path 230) from a user's finger in contact with the input surface to other components of the electronic device.

The switch module 216 may include a conductive dome 240 and a friction guard 250 that is positioned between the conductive dome 240 and the actuation member 212 of the crown assembly 210. The conductive dome 240 and/or the friction guard 250 may define at least a portion of the conductive path 230 from the input surface 214 to the processing unit 220.

The conductive dome 240 and/or the friction guard 250 may provide an outward biasing force that maintains the actuation member in an unactuated position shown in FIG. 2B absent an inward force on the actuation member. The outward biasing force may include a spring force exerted by the conductive dome 240 and/or the friction guard 250 on the actuation member 212.

Figure 2C:
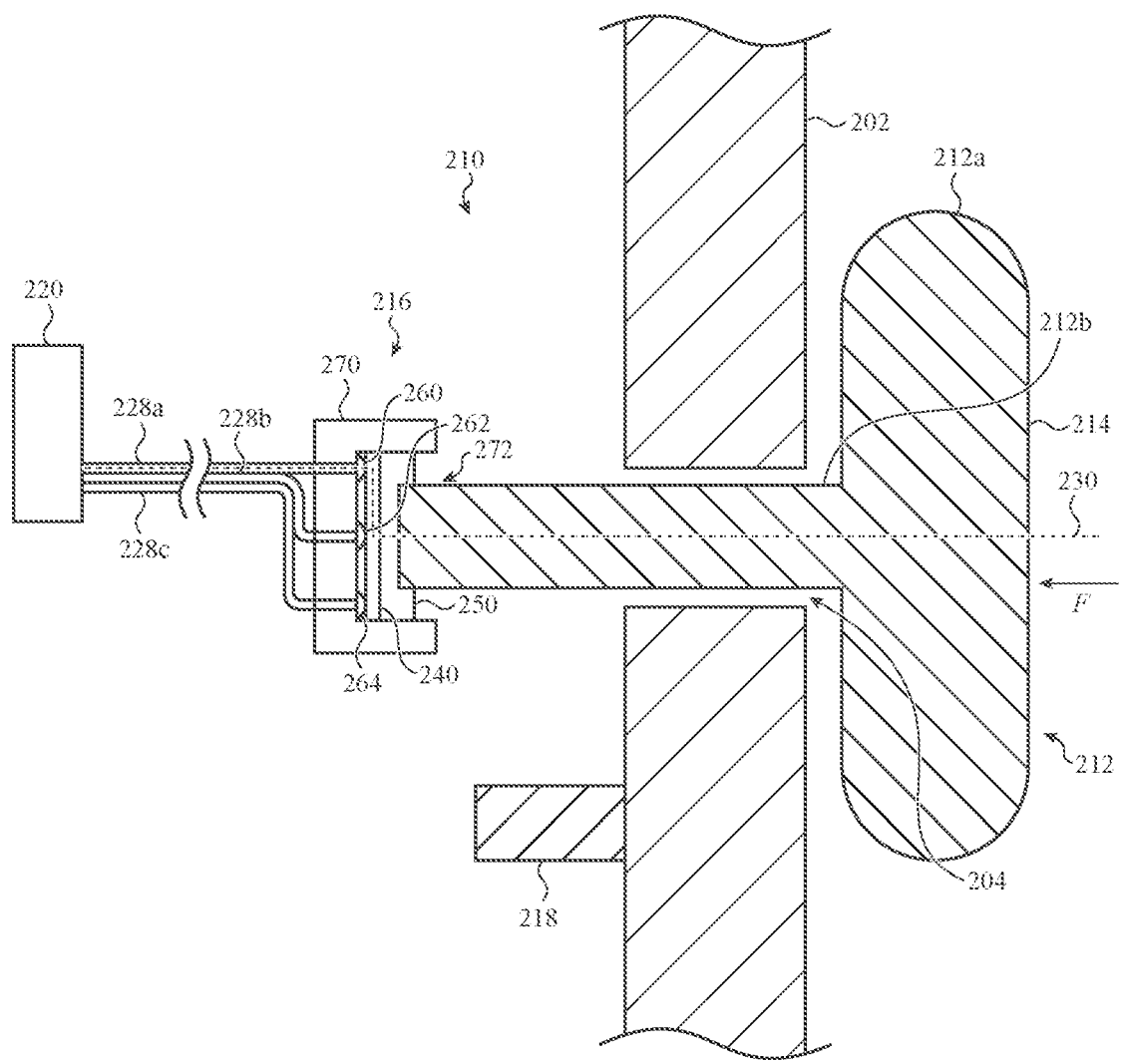

As noted herein, the crown assembly 210 may receive translational inputs that cause the actuation member 212 to translate inward from the unactuated position to an actuated position. FIG. 2C depicts the actuation member 212 of the crown assembly 210 in the actuated position in response to a translational input on the actuation member 212. A translational input may be provided to the crown assembly 210 in the form of an inward force F that overcomes the outward biasing force provided by the conductive dome 240 and/or the friction guard 250 and causes the actuation member 212 to translate inward to the actuated position shown in FIG.

2C. When the inward force F is removed or reduced, the outward biasing force may cause the actuation member 212 to return to the unactuated position shown in FIG. 2B.

The conductive dome 240 may collapse in response to the translational input moving the actuation member 212 from the unactuated position to the actuated position. As shown in FIG. 2B, when the actuation member 212 is in the unactuated position, the conductive dome 240 is in an uncollapsed configuration. As shown in FIG. 2C, when the actuation member 212 is in the actuated position, the conductive dome 240 is in a collapsed configuration.

At least a portion of the conductive dome 240 may be conductively coupled to a persistent electrical contact 260 that forms at least a portion of the conductive path 230 from the input surface 214 to the processing unit 220. The persistent electrical contact 260 may be conductively coupled to the processing unit 220, for example by a connector 228a, to facilitate transmission of signals between the input surface 214 and the processing unit. The conductive dome 240 may be in direct contact with the persistent electrical contact 260. The conductive dome 240 may contact the persistent electrical contact 260 while the conductive dome is in the uncollapsed configuration, the collapsed configuration, and positions therebetween so that the conductive coupling between the input surface 214 and the processing unit 220 may be maintained regardless of the position of the actuation member 212.

As shown in FIG. 2C, in the collapsed configuration, the conductive dome 240 may contact a switch electrical contact 262. The conductive dome 240 contacting the switch electrical contact 262 may conductively couple at least a portion of the conductive dome 240 to the switch electrical contact 262, which may close a circuit to register a translational input. The circuit may include and/or be operably coupled to the processing unit 220, for example via a connector 228b.

In the uncollapsed configuration and/or the collapsed configuration, the conductive dome 240 may contact a reference electrical contact 264 that provides a bias voltage for detecting translational inputs and/or input signals at the input surface 214. The reference electrical contact 264 may be operably coupled to the processing unit 220, for example by a connector 228c. The conductive dome 240 contacting the switch electrical contact 262 may close a circuit that includes the reference electrical contact 264, which may register a translational input. The circuit may include and/or be operably coupled to the processing unit 220, for example via connectors 228b and 228c.

The conductive dome 240 may be a unitary piece of conductive material that is able to collapse and return to an uncollapsed configuration thereafter. The conductive dome 240 may include multiple pieces, such as layers. In some cases, the conductive dome 240 is substantially homogeneous, meaning it has consistent materials throughout its entire volume. The conductive dome 240 may be formed of any suitable conductive material or combination of materials (e.g., metal, carbon fiber, conductive polymer, conductive ceramics, or the like).

The conductive dome 240 may define one or more conductive routes that are electrically isolated from one another. The conductive dome 240 may include vias or other structural elements for defining the isolated conductive routes. The conductive dome 240 may define a first conductive route between the friction guard 250 and the persistent electrical contact 260 that forms at least a portion of the conductive path 230. The conductive dome 240 may define a second conductive route between the switch electrical contact 262 and the reference electrical contact 264 that forms a part of the circuit for detecting translational inputs. The first and second conductive routes may be electrically isolated from one another to prevent signal interference. In some cases, the conductive dome 240 does not define separate conductive routes. That is to say, the conductive route between the friction guard 250 and the persistent electrical contact 260 that forms at least a portion of the conductive path 230 is not electrically isolated from the conductive route between the switch electrical contact 262 and the reference electrical contact 264 that forms a part of the circuit for detecting translational inputs.

The friction guard 250 may be positioned between the actuation member 212 and the conductive dome 240, and may protect the conductive dome 240 or other components of the switch module 216 from damage resulting from contacting the actuation member 212. For example, the friction guard 250 may protect the conductive dome 240 from shearing forces resulting from rotation of the actuation member 212. As noted herein, the friction guard 250 may form part of the conductive path 230. The friction guard 250 may be formed of any suitable conductive material or combination of materials (e.g., metal, carbon fiber, conductive polymer, conductive ceramics, or the like). In some cases, the friction guard 250 may be omitted or integrated with the conductive dome 240.

As noted herein, the conductive dome 240 and/or the friction guard 250 may provide an outward biasing force that maintains the actuation member in an unactuated position shown in FIG. 2B. In embodiments in which the friction guard 250 provides at least a portion of the outward biasing force, the friction guard may include one or more flexures that provide the outward biasing force. As described in more detail below with respect to FIGS. 4A-5C, the friction guard 250 may maintain a gap between the friction guard and the conductive dome 240 when the actuation member 212 is in the unactuated position and/or for at least a portion of the transition to the actuated position such that the friction guard 250 provides the outward biasing force. During the transition from the unactuated position to the actuated position, the friction guard 250 may come into contact with the conductive dome 240 or otherwise cause the force exerted on the actuation member 212 to be transferred to the conductive dome 240, thereby causing the dome to collapse.

The switch module 216 may include a switch housing 270 that at least partially surrounds one or more components of the switch module 216. The housing 270 may define a recess 272 in which the conductive dome 240, the friction guard 250, and/or one or more of the electrical contacts 260, 262, 264 are positioned. The switch housing 270 may include a bracket or other fastening component for coupling the switch module 216 to the enclosure 202 or one or more other components of the electronic watch 200. In some cases, the electrical contacts 260, 262, 264 may be encapsulated within the switch housing 270. For example, the electrical contacts may be formed as part of a base of the switch housing 270 by injection molding.

As shown in FIG. 2B, the crown assembly 210 may include a rotation sensor 218 positioned along a side of the crown shaft 212b or at another suitable location. The rotation sensor 218 may have similar structure or functionality as the rotation sensors discussed herein (e.g., rotation sensor 118). The processing unit 220 may have similar structure or functionality as the processing units discussed herein (e.g., processing unit 120 of FIG. 1).

Figure 3A:
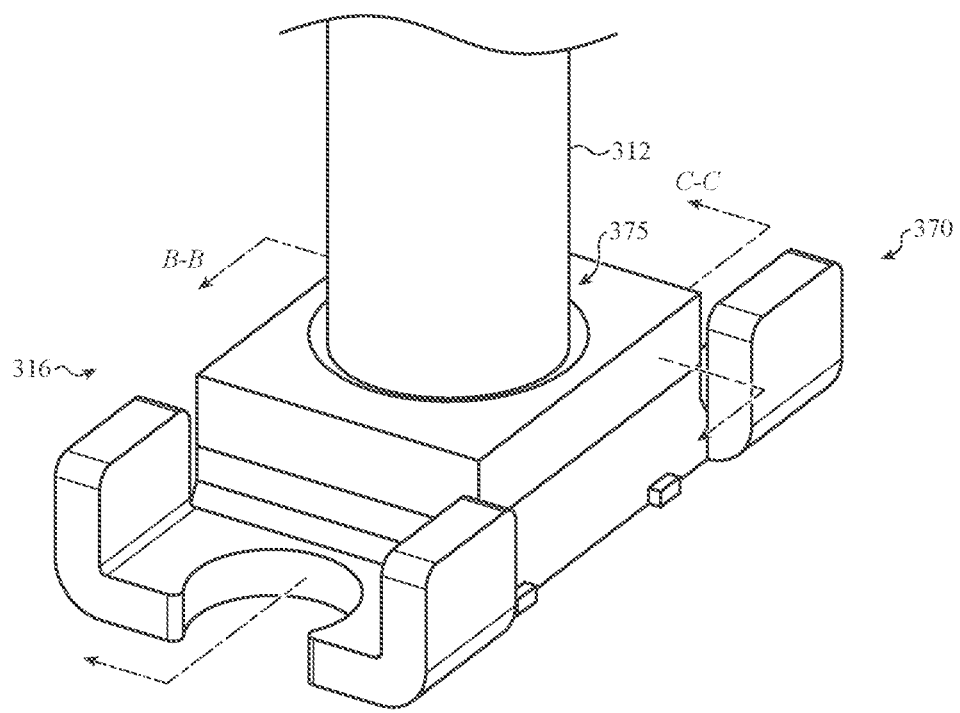
FIG. 3A-3F show an example switch module for an electronic device.

FIG. 3A shows an example switch module 316 for an electronic device. The switch module 316 may be part of a crown assembly (e.g., crown assembly 110, 210) for an electronic device (e.g., electronic device 100, 200). The switch module 316 may include a housing 370 that defines an opening 375 through which an actuation member 312 may partially extend. The switch module 316 may detect movement of the actuation member 312 to detect translational inputs, and the switch module may define at least a portion of a conductive path between the actuation member 312 and a processing unit.

Figure 3B:
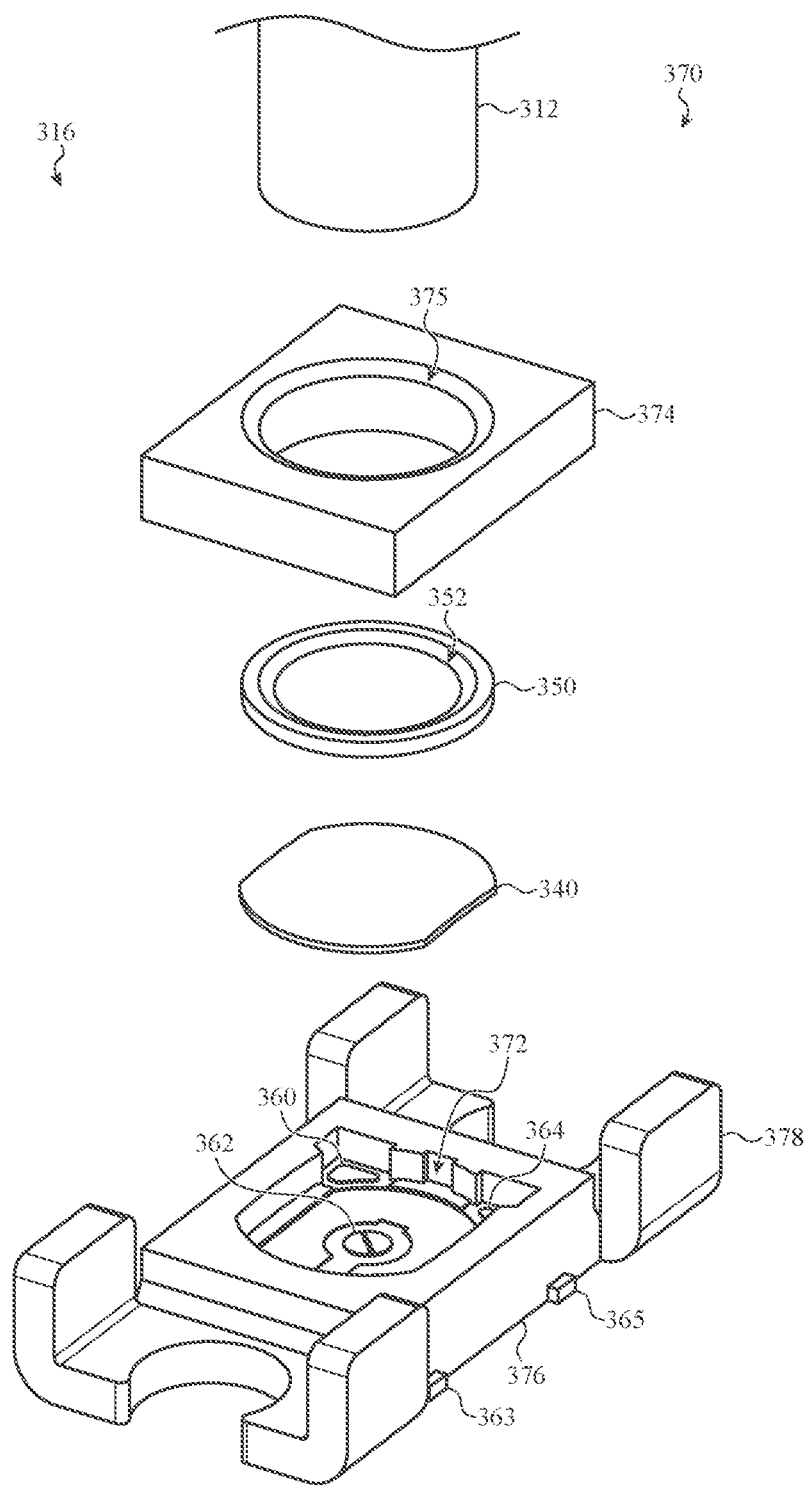

FIG. 3B shows an exploded view of the example switch module 316. As shown in FIG. 3B, the switch module 316 includes a conductive dome 340 and friction guard 350 that are positioned at least partially within a switch housing formed by a cover 374 and a base 376. The cover 374 may be coupled to the base 376. The base 376 may define a recess 372 in which a persistent electrical contact 360, a switch electrical contact 362, and a reference electrical contact 364 are located. The conductive dome 340 may be positioned in the recess 372. Each electrical contact 360, 362, 364 may be defined by and/or conductively coupled to a conductive member (e.g., conductive members 363, 365) that may contact a connector when the switch module 316 is installed in the electronic watch to conductively couple the respective electrodes to a processing unit or other circuitry. The switch electrical contact 362 may be positioned in a center region of the recess 372. The persistent electrical contact 360 and/or the reference electrical contact 364 may be positioned in a peripheral region of the recess 372 that surrounds the central region. The switch electrical contact 362 may contact a center portion of the conductive dome 340 when the conductive dome collapses. The persistent electrical contact 360 may contact a peripheral portion of the conductive dome 340 that surrounds the center portion.

The cover 374 and the base 376 may be formed of any suitable material or combination of materials, including metals, polymers, ceramics and the like. In some cases, the cover 374 is formed of a non-conductive material, such as a polymer, to electrically isolate the actuation member 312, the friction guard 350, and or the conductive dome 340 from other components of the switch module 316 or the electronic device. The base 376 may include a non-conductive material, such as a polymer, surrounding conductive material, such as metal, that forms the electrical contacts 360, 362, 364, and/or the conductive members 363, 365. In some cases, the electrical contacts 360, 362, 364, and/or the conductive members 363, 365 are encapsulated within the base 376, for example by injection molding.

The switch housing 370 may include a bracket 378 for attaching the switch module 316 to the electronic watch. The bracket 378 may be formed of any suitable material or combination of materials, including metals, polymers, ceramics and the like. In some cases, the bracket 378 includes one or more metals, and the base 376 is attached to the bracket by molding the base around the bracket.

The cover 374 may define an opening 375 that the actuation member 312 may extend at least partially through. The cover 374 may extend around the actuation member 312. The cover 374 may retain the conductive dome 340 and/or the friction guard 350 within the recess 372. The friction guard 350 may be aligned with the opening such that the actuation member 312 contacts the friction guard. The friction guard 350 may include a recess 352 for receiving the actuation member 312 and preventing lateral movement of the actuation member.

Figure 3C:
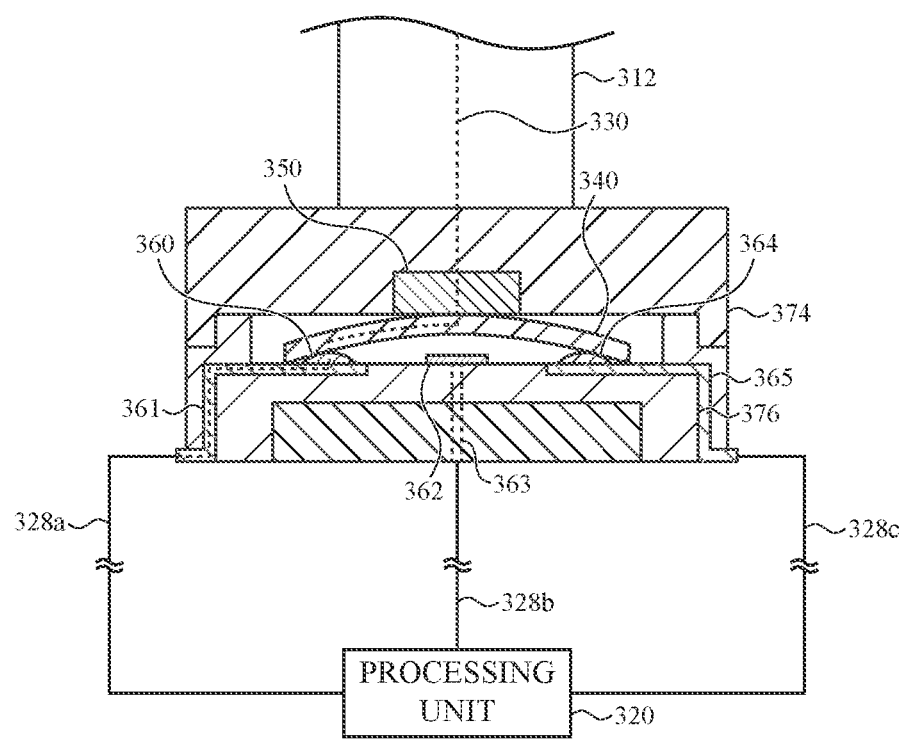
Figure 3D:
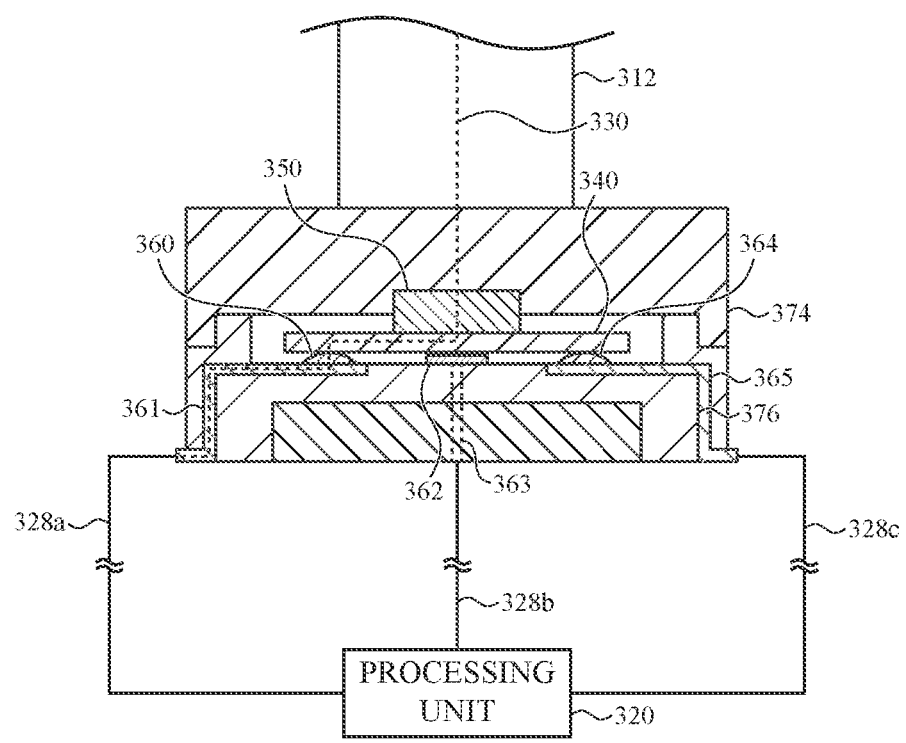

FIGS. 3C and 3D are example cross-section views of the switch module 316, taken through section line B-B of FIG. 3A. FIG. 3C shows the actuation member 312 in an unactuated position and the conductive dome 340 in an uncollapsed configuration. FIG. 3D shows the actuation member 312 in an actuated position and the conductive dome 340 in a collapsed configuration, for example in response to a force applied to the actuation member 312. The conductive dome 340 may provide an outward biasing force that maintains the actuation member 312 in the unactuated position absent an inward force on the actuation member.

As noted herein, the friction guard 350 and the conductive dome 340 may define at least a portion of a conductive path 330 from an input surface of the actuation member 312 to a processing unit 320 of the electronic device. The persistent electrical contact 360 may also define a portion of the conductive path 330 between the input surface of the actuation member 312 and the processing unit 320. As shown in FIGS. 3C and FIG. 3D, the conductive dome 340 contacts the persistent electrical contact 360 in the uncollapsed configuration and the collapsed configuration, such that the conductive path 330 is maintained whether the actuation member 312 is in the unactuated position or the actuated position. The persistent electrical contact 360 may be defined by and/or conductively coupled to a conductive member 361 that extends through the base 376. The conductive member 361 may be conductively coupled to the processing unit 320, for example by a connector 328*a*. As noted above, the persistent electrical contact 360 and/or the conductive member 361 may be encapsulated within the base 376, for example by injection molding.

As shown in FIG. 3C, when the actuation member 312 is in the unactuated position, the conductive dome 340 is in the uncollapsed configuration and the conductive dome does not contact the switch electrical contact 362. As shown in FIG. 3D, when the actuation member 312 is in the actuated position, for example in response to an inward force applied to the actuation member 312, the conductive dome 340 is in the collapsed configuration and contacts the switch electrical contact 362, which may close a circuit that includes the switch electrical contact 362 and the reference electrical contact 364 to register a translational input. The switch electrical contact 362 may be defined by and/or conductively coupled to a conductive member 363 that extends through the base 376. The conductive member 363 may be conductively coupled to the processing unit 320, for example by a connector 328*b*. The reference electrical contact 364 may be defined by and/or conductively coupled to a conductive member 365 that extends through the base 376. The conductive member 365 may be conductively coupled to the processing unit 320, for example by a connector 328*c*.

Figure 3E:
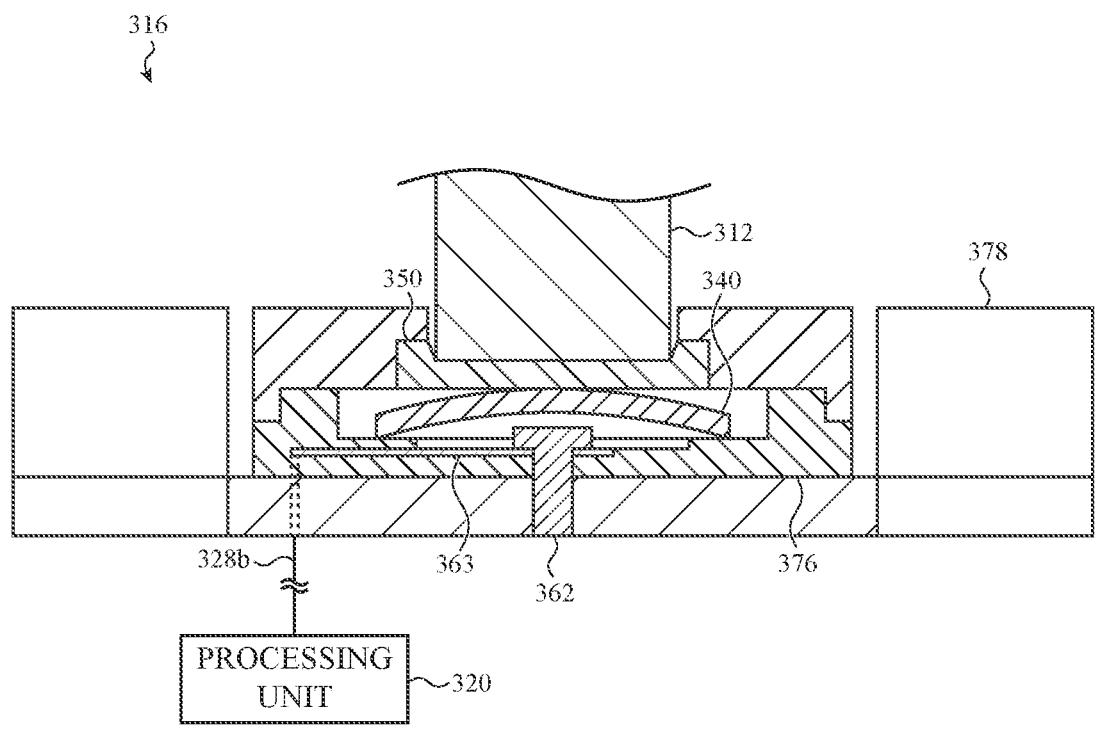
Figure 3F:
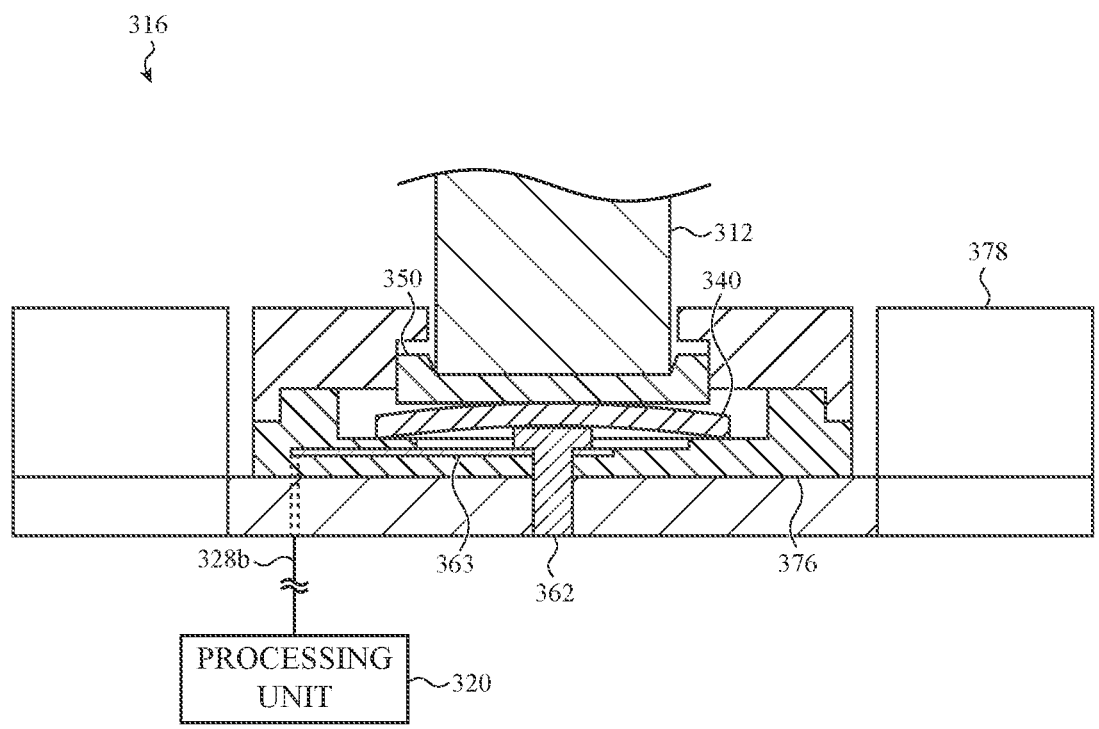

FIGS. 3E and 3F are example cross-section views of the switch module 316, taken through section line C-C of FIG. 3A. FIG. 3E shows the actuation member 312 in the unactuated position and the conductive dome 340 in the uncollapsed configuration. FIG. 3F shows the actuation member 312 in the actuated position and the conductive dome 340 in the collapsed configuration, for example in response to a force applied to the actuation member 312. As shown in FIG. 3E, when the actuation member 312 is in the unactuated position, the conductive dome 340 is in the uncollapsed configuration and the conductive dome does not contact the switch electrical contact 362. As shown in FIG. 3F, when the actuation member 312 is in the actuated position, for example in response to an inward force applied to the actuation member 312, the conductive dome 340 is in the collapsed configuration and contacts the switch electrical contact 362 to register a translational input.

Figure 4A:
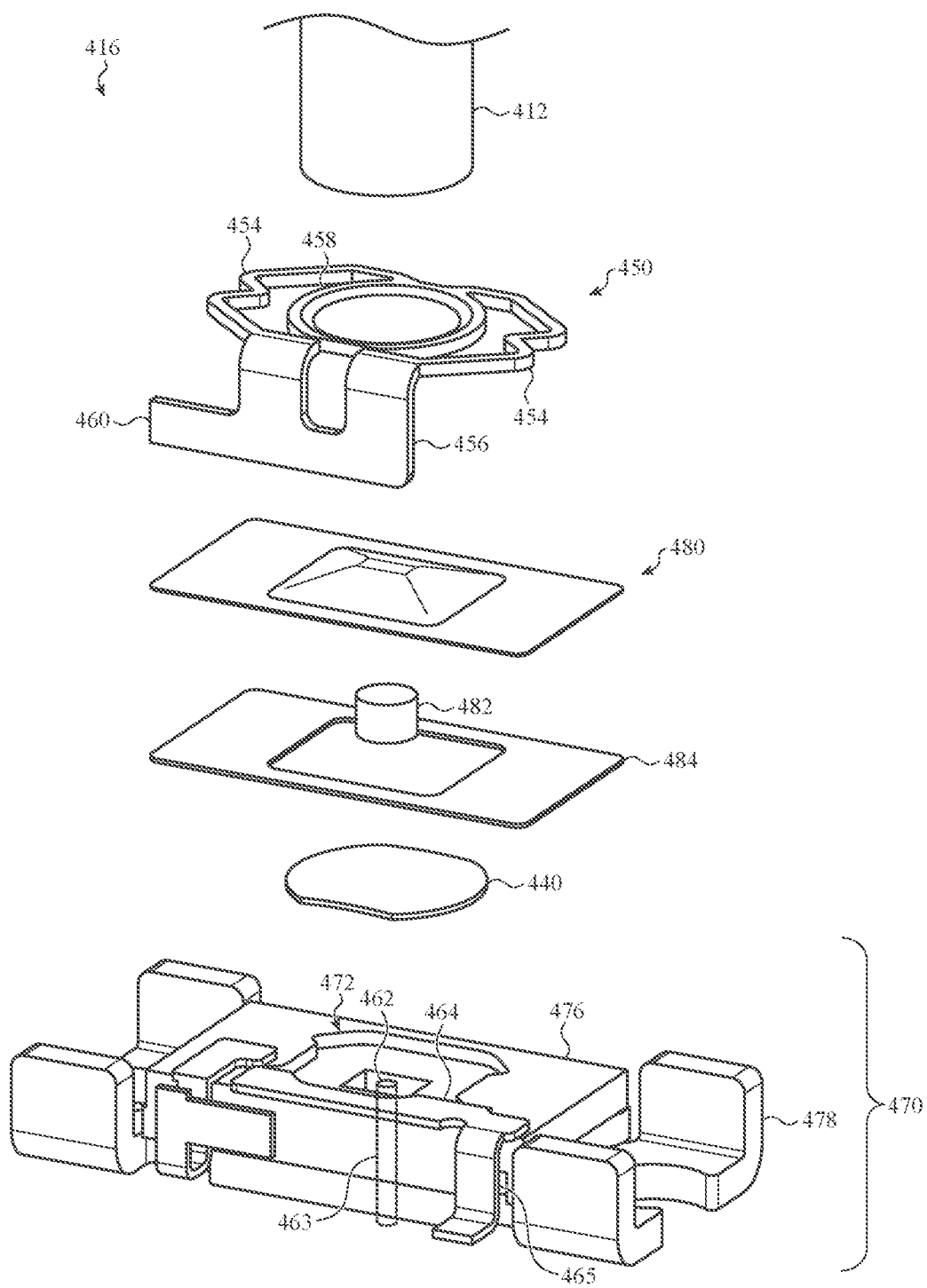
FIGS. 4A-4C show an example switch module for an electronic device.
Figure 4B:
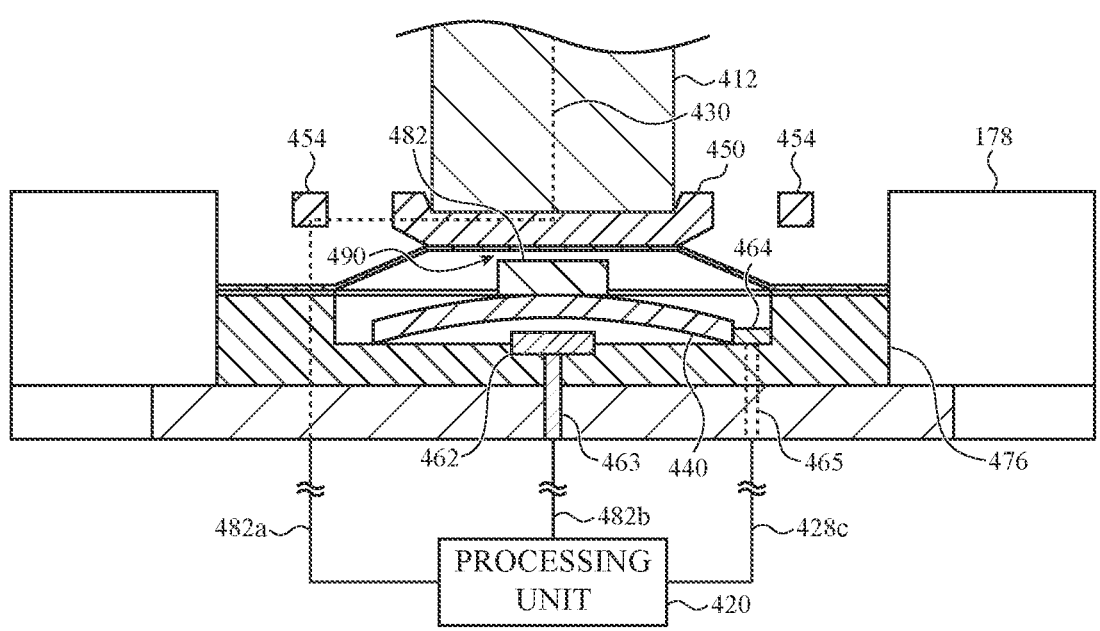
Figure 4C:
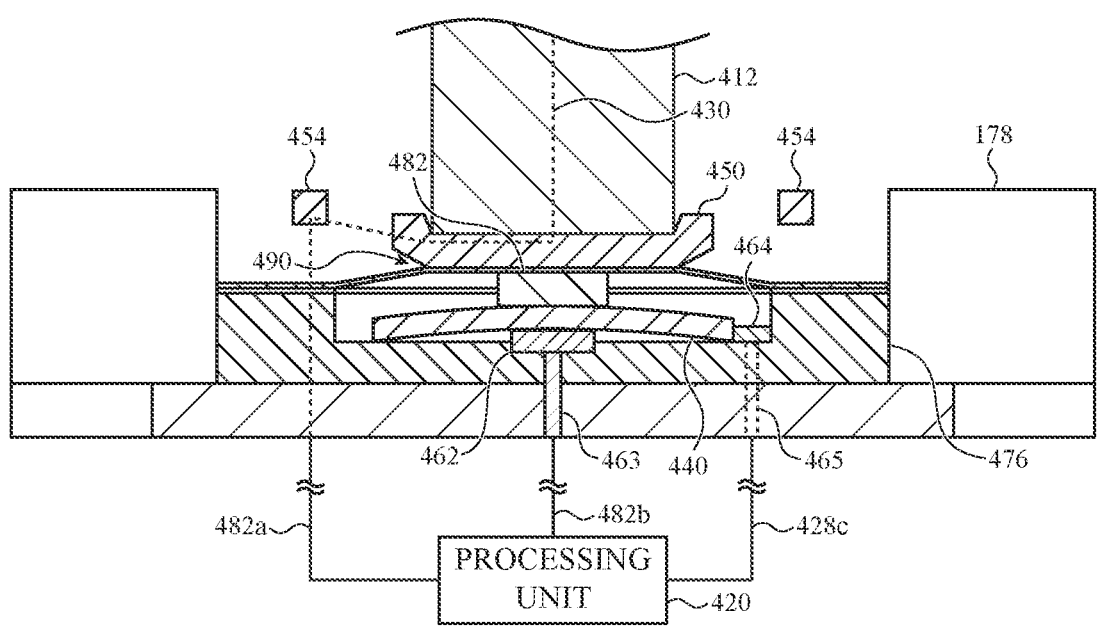

FIGS. 4A-4C show an example switch module 416 for an electronic device. The switch module 416 may be part of a crown assembly (e.g., crown assembly 110, 210) for an electronic device (e.g., electronic device 100, 200). FIG. 4A shows an exploded view of the switch module 416.

The switch module 416 may include a friction guard 450. As noted herein, the friction guard 450 may provide an outward biasing force that maintains the actuation member in an unactuated position. The friction guard 450 may include a translating portion 458 and one or more flexures 454 that allow the translating portion 458 to move relative to the switch housing. The friction guard 450 may be attached to the base 476 via a support member 456. The flexures 454 may extend from the support member 456 and at least partially surround the translating portion 458 of the friction guard 450. The translating portion 458 may be adapted to receive the actuation member 412. The actuation member 412 may contact the translating portion 458, and the translating portion may translate relative to the support member 456 and the base 476 to allow translation of the actuation member. The friction guard 450 may act as a spring, with the flexures 454 exerting a reaction force on the translating portion 458 (and therefore on the actuation member 412) that is dependent on the position of the translating portion. The spring dynamics of the friction guard 450 may be defined by the material properties, the thickness, and the length of the flexures 454. In some cases, as shown in FIG. 4A, the flexures 454 may be M-shaped flexures. This may allow the flexures to have a sufficient length to provide a desired outward biasing force while minimizing or reducing the size of the friction guard 450. Minimizing or reducing the size of the friction guard may reduce the size of the switch module 416, which may reduce a size of a device that the switch module is installed in.

As described herein, the friction guard 450 may define at least a portion of a conductive path from the actuation member 412 to a processing unit. In some cases, the flexures 454 may define a portion of the conductive path. For example, the actuation member 412 may contact the translating portion 458 of the friction guard, and a conductive path may extend from the translating portion 458, through one or both flexures 454, and through the support member 456 to a conductive member 460 extending from the support member 456. The conductive member 460 may be conductively coupled to a connector that is conductively coupled to a processing unit or another circuit of the electronic device.

The switch module 416 may include a housing 470 that includes a base 476 and a bracket 478 for attaching the switch module 416 to the electronic device. The base 476 may define a recess 472, and a conductive dome 440 may be positioned in the recess. A switch electrical contact 462 and a reference electrical contact 464 for detecting translational inputs may be positioned at least partially in the recess 472. Each electrical contact 462, 464 may be defined by and/or conductively coupled to a conductive member 463, 465 that may contact a connector when the switch module 416 is installed in the electronic watch to conductively couple the respective electrical contacts to a processing unit or other circuitry.

The housing 470 may include a flexible cover 480 attached to the base using an adhesive 484 (e.g., a pressure-sensitive adhesive or heat-sensitive adhesive). The flexible cover 480 and/or a spacer 482 may electrically isolate the friction guard 450 and the conductive dome 440 so that signals related to sensing translational inputs at the conductive dome 440 do not interfere with signals from the actuation member 412 being transmitted through the friction guard 450.

The base 476 may be formed of any suitable material or combination of materials, including metals, polymers, ceramics and the like. The base 476 may include a non-conductive material, such as a polymer, surrounding conductive material, such as metal, that forms the electrical contacts 462, 464, and/or the conductive members 463, 465. In some cases, the electrical contacts 462, 424, and/or the conductive members 463, 465 are encapsulated within the base 476, for example by injection molding.

FIGS. 4B and 4C are example cross-section views of the switch module 416. FIG. 4B shows the actuation member 412 in an unactuated position and the friction guard 450 and the conductive dome 440 in an uncollapsed configuration. FIG. 4C shows the actuation member 412 in an actuated position and the friction guard 450 and the conductive dome 440 in a collapsed configuration, for example in response to a force applied to the actuation member 412. The friction guard 450 may provide an outward biasing force that maintains the actuation member 412 in the unactuated position shown in FIG. 4B absent an inward force on the actuation member.

The friction guard 450 may maintain a gap 490 between the friction guard and the conductive dome 440 when the actuation member 412 is in the unactuated position and/or for at least a portion of the transition to the actuated position such that the friction guard provides the outward biasing force on the actuation member 412. During the transition from the unactuated position to the actuated position, the friction guard 450 may come into contact with the spacer 482 or otherwise cause the force exerted on the actuation member 412 to be transferred to the conductive dome 440, thereby causing the dome to collapse.

As shown in FIGS. 4B and 4C, the conductive path 430 may be maintained when the actuation member 412 is in the unactuated position, the actuated position, and positions therebetween. The friction guard 450 may be conductively coupled to the processing unit, for example by a connector 428a. The conductive path 430 may be electrically isolated from the conductive dome so that signals used to detect translational inputs do not interfere with the signals from the actuation member 412.

As shown in FIG. 4B, when the actuation member 412 is in the unactuated position, the conductive dome 440 is in the uncollapsed configuration and the conductive dome does not contact the switch electrical contact 462. As shown in FIG. 4C, when the actuation member 412 is in the actuated position, for example in response to an inward force applied to the actuation member 412, the conductive dome 440 is in the collapsed configuration and contacts the switch electrical contact 462, which may close a circuit that includes the switch electrical contact 462 and the reference electrical contact 464 to register a translational input. The switch electrical contact 462 may be defined by and/or conductively coupled to a conductive member 463 that extends through the base 476. The conductive member 463 may be conductively coupled to the processing unit 420, for example by a connector 428b. The reference electrical contact 464 may be defined by and/or conductively coupled to a conductive member 465 that extends through the base 476. The conductive member 465 may be conductively coupled to the processing unit 420, for example by a connector 428c.

Figure 5A:
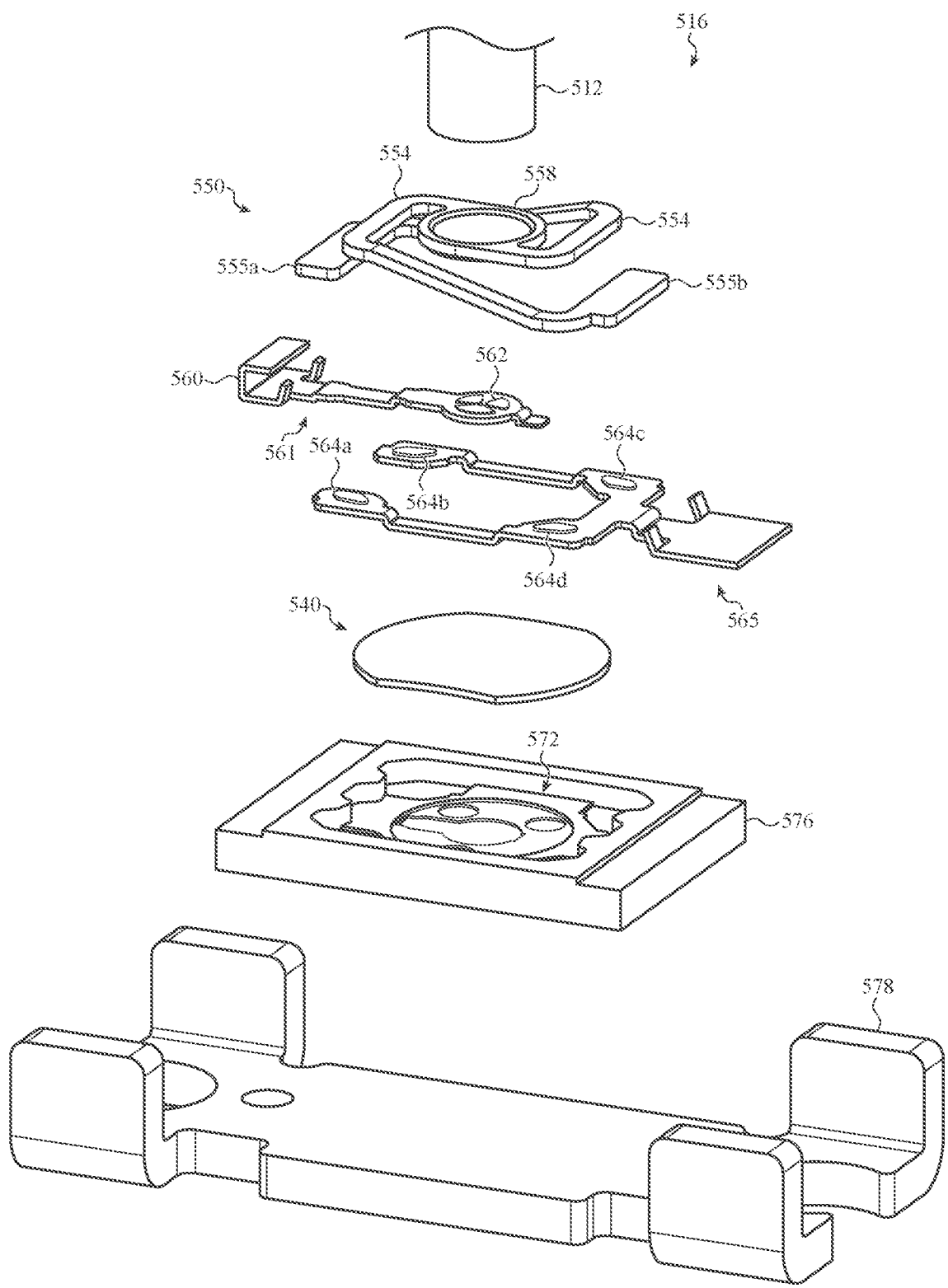
FIGS. 5A-5C show an example switch module for an electronic device.
Figure 5B:
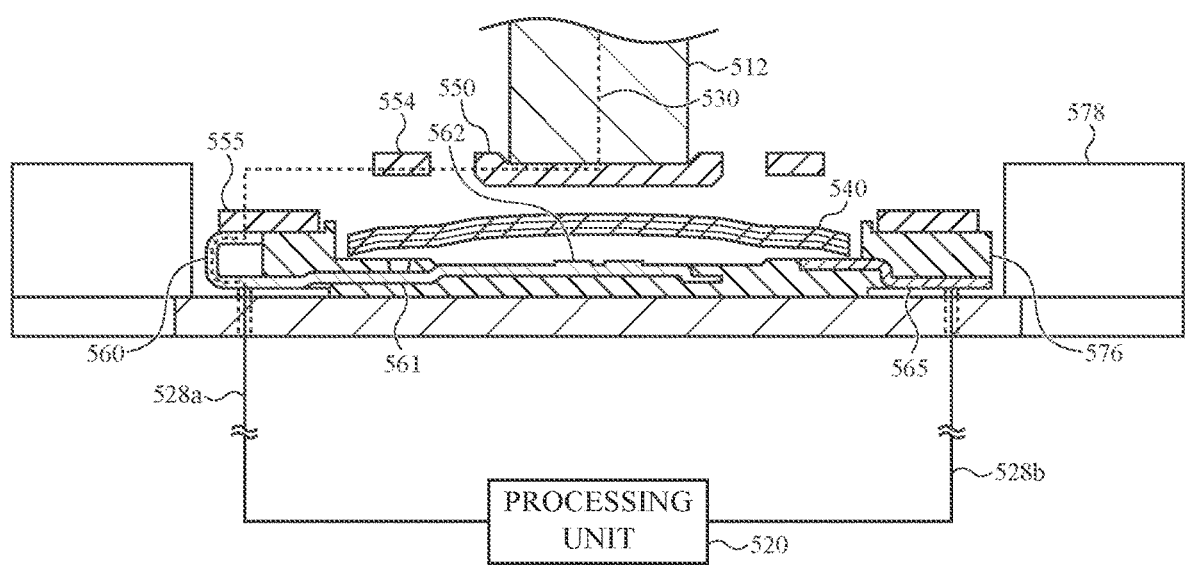
Figure 5C:
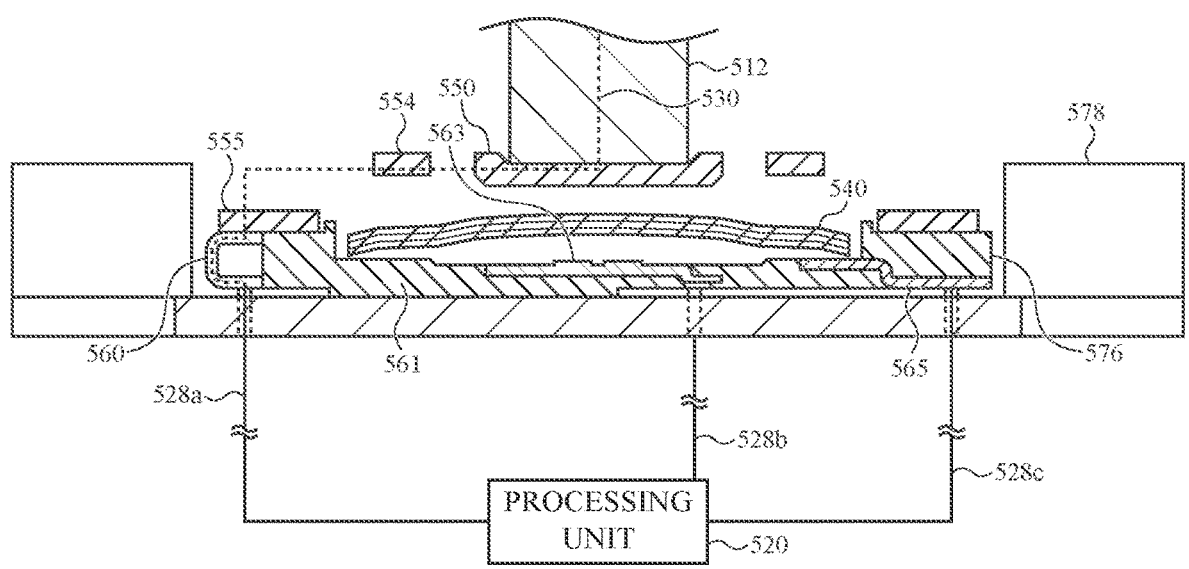

FIGS. 5A-5C show an example switch module 516 for an electronic device. The switch module 516 may be part of a crown assembly (e.g., crown assembly 110, 210) for an electronic device (e.g., electronic device 100, 200). FIG. 5A shows an exploded view of the switch module 516. FIG. 5B is a first example cross-section view of the switch module 516. FIG. 5C is a second example cross-section view of the switch module 516.

The switch module 516 may include a friction guard 550. Similar to the friction guard 450 discussed with respect to FIGS. 4A-4C, the friction guard 550 may provide an outward biasing force that maintains the actuation member 512 in an unactuated position. The friction guard 550 may act as a spring, and may include one or more flexures 554 that define the spring dynamics of the friction guard. The friction guard 550 may be attached to the base 576 via support members 555a, 555b. Each flexure 554 may extend from a support member 555a, 555b and at least partially surround a translating portion 558 of the friction guard 550. The actuation member 512 may contact the translating portion 558, and the translating portion may translate relative to the support members 555a, 555b and the base 576 to allow translation of the actuation member. The spring dynamics of the friction guard 550 may be defined by the material properties, the thickness, and the length of the flexures 554. In some cases, as shown in FIG. 5A, the flexures 554 may be U-shaped flexures. This may allow the flexures 554 to have a sufficient length to provide a desired outward biasing force while minimizing or reducing the size of the friction guard 550. Minimizing or reducing the size of the friction guard 550 may reduce the size of the switch module 516, which may reduce a size of a device that the switch module is installed in.

As shown in FIGS. 5B and 5C, the friction guard 550 may define at least a portion of a conductive path 530 from the actuation member 512 to a processing unit 520. In some cases, one or more of the flexures 554 may define a portion of the conductive path. For example, the actuation member 512 may contact the translating portion 558 of the friction guard, and the conductive path 530 may extend from the translating portion 558, through a flexure 554, and through the support member 555a. The support member 555a may be conductively coupled to a persistent electrical contact 560 that is defined by and/or conductively coupled to a conductive member 561 that may be conductively coupled to the processing unit 520 or another circuit of the electronic device.

The switch module 516 may include a housing 570 that includes a base 576 and a bracket 578 for attaching the switch module 516 to the electronic device. The base 576 may define a recess 572, and a conductive dome 540 may be positioned in the recess. A switch electrical contact 562 and reference electrical contacts 564a-d for detecting translational inputs may be positioned at least partially in the recess 572. In some cases, the persistent electrical contact 560 and the switch electrical contact 562 may share a common conductive member (e.g., conductive member 561) such that they are conductively coupled to one another. As shown in FIGS. 5A and 5B, the switch electrical contact 562 and the persistent electrical contact 560 may be conductively coupled to the processing unit 520 via the conductive member 561 and the connector 528a. This may reduce a number of conductive paths from the switch module 516 to the processing unit 520. Each electrical contact 564a-d may be defined by and/or conductively coupled to a conductive member 565 that may contact a connector when the switch module 516 is installed in the electronic watch to conductively couple the electrical contact to a processing unit or other circuitry.

In some cases, the persistent electrical contact 560 and the switch electrical contact 562 may have separate conductive members that are electrically isolated from one another. As shown in FIG. 5C, the persistent electrical contact 560 may be defined by and/or conductively coupled to the conductive member 561, which is conductively coupled to the processing unit 520 via the connector 528a. The switch electrical contact 562 may be defined by and/or conductively coupled to a conductive member 563, which is conductively coupled to the processing unit 520 via a connector 528b.

Figure 6A:
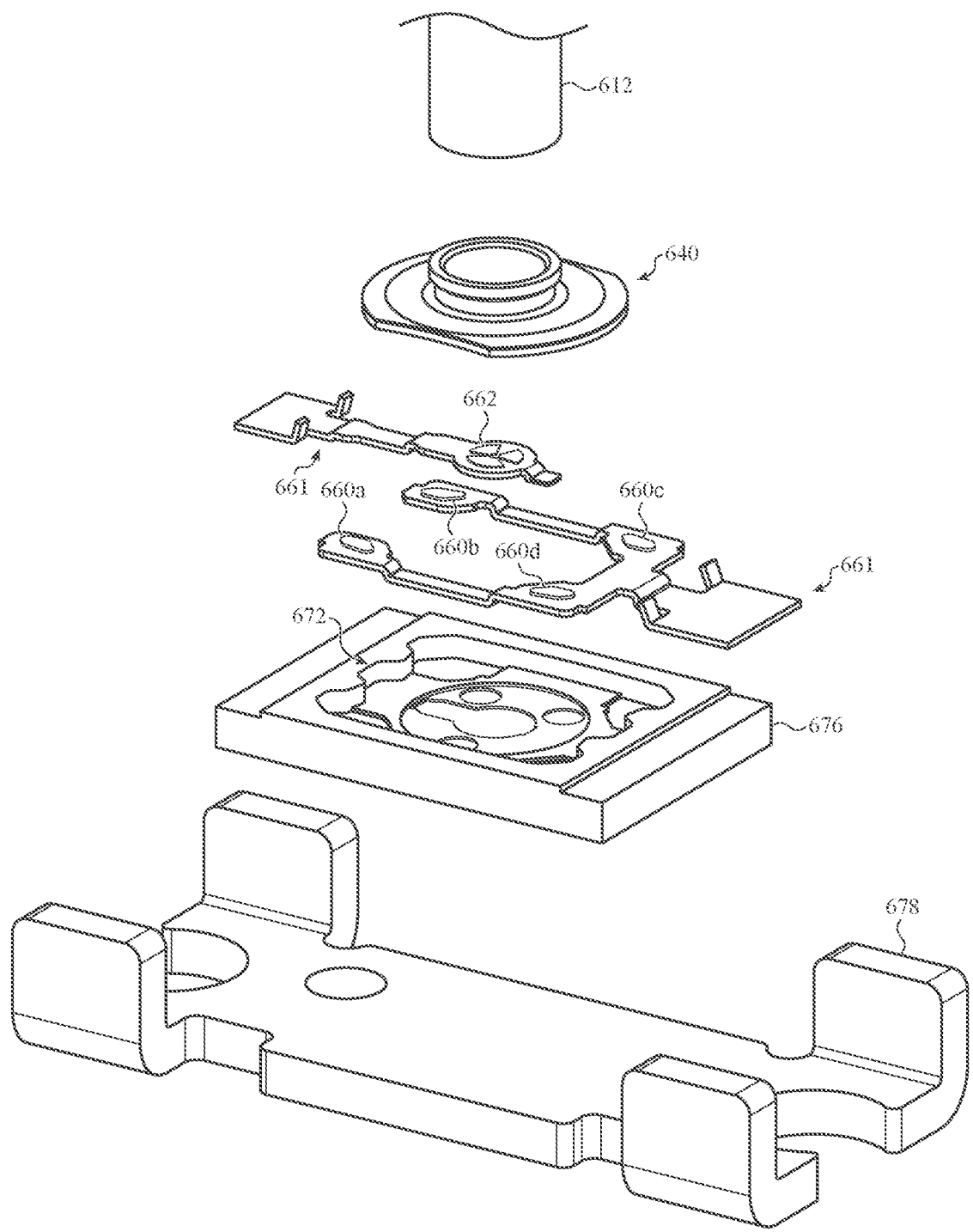
FIGS. 6A-6B show an example switch module for an electronic device.
Figure 6B:
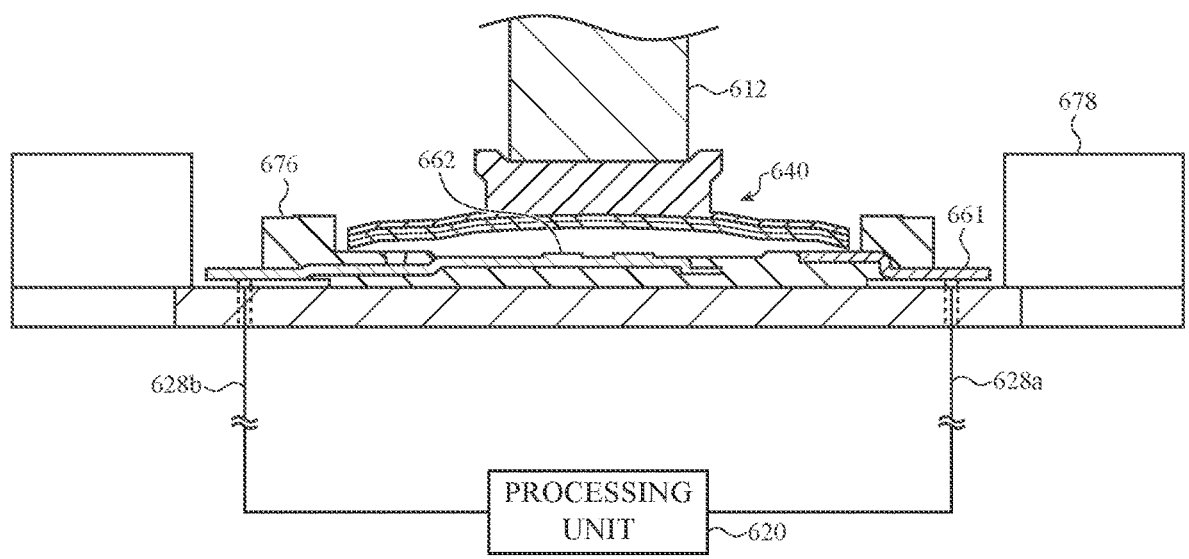

As shown in FIGS. 5A-5C, a switch module may have a friction guard and a conductive dome that are separate components. In some embodiments, the friction guard and the conductive dome of a switch module may be formed as a single component. FIGS. 6A-6B show an example switch module 616 for an electronic device in which a conductive dome 640 and a friction guard 650 are formed as a single component. Forming the conductive dome 640 and the friction guard 650 as a single component may reduce the size of the switch module 616, which may reduce a size of a device that the switch module is installed in and may simplify manufacturing by reducing a number of components. The switch module 616 may be part of a crown assembly (e.g., crown assembly 110, 210) for an electronic device (e.g., electronic device 100, 200). FIG. 6A shows an exploded view of the switch module 616. FIG. 6B is an example cross-section view of the switch module 616. The switch module 616 may be similar to the switch module 516 discussed with respect to FIGS. 5A-5C.

As shown in FIG. 6B, the conductive dome 640 and friction guard 650 may define at least a portion of a conductive path 630 from an actuation member 612 to a processing unit 620. The conductive dome 640 and friction guard 650 may provide an outward biasing force that maintains the actuation member 612 in an unactuated position.

The conductive dome 640 may be positioned in a recess 672 of a base 676 of the switch module 616. The conductive dome 640 may contact persistent electrical contacts 660a-d, one or more of which form at least a portion of the conductive path 630. Each persistent electrical contact 660a-d may be defined by and/or conductively coupled to a conductive member 661, which is conductively coupled to the processing unit 620 via a connector 628a. The conductive dome 640 may be configured to collapse in response to a translational movement of the actuation member 612, causing the conductive dome to contact a switch electrical contact 662 to register a translational input. The switch electrical contact may be defined by and/or conductively coupled to a conductive member 663, which is conductively coupled to the processing unit 620 via a connector 628b.

Figure 7:
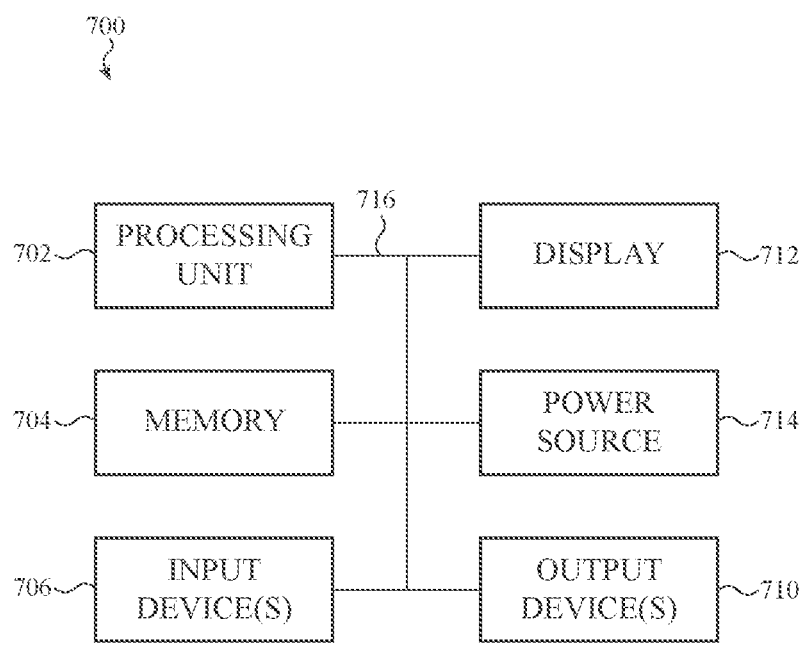
FIG. 7 shows a sample electrical block diagram of an electronic device that may incorporate a switch module.

FIG. 7 shows a sample electrical block diagram of an electronic device 700 that may incorporate a switch module. The electronic device may in some cases take the form of any of the electronic devices described with reference to FIGS. 1-6B, or other portable or wearable electronic devices. The electronic device 700 can include a display 712 (e.g., a light-emitting display), a processing unit 702, a power source 714, a memory 704 or storage device, an input device 706 (e.g., a crown assembly), and an output device 710.

The processing unit 702 can control some or all of the operations of the electronic device 700. The processing unit 702 can communicate, either directly or indirectly, with some or all of the components of the electronic device 700. For example, a system bus or other communication mechanism 716 can provide communication between the processing unit 702, the power source 714, the memory 704, the input device(s) 706, and the output device(s) 710.

The processing unit 702 can be implemented as any electronic device capable of processing, receiving, or transmitting data or instructions. For example, the processing unit 702 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 700 can be controlled by multiple processing units. For example, select components of the electronic device 700 (e.g., an input device 706) may be controlled by a first processing unit and other components of the electronic device 700 (e.g., the display 712) may be controlled by a second processing unit, where the first and second processing units may or may not be in communication with each other. In some cases, the processing unit 702 may determine a biological parameter of a user of the electronic device, such as an ECG for the user.

The power source 714 can be implemented with any device capable of providing energy to the electronic device 700. For example, the power source 714 may be one or more batteries or rechargeable batteries. Additionally or alternatively, the power source 714 can be a power connector or power cord that connects the electronic device 700 to another power source, such as a wall outlet.

The memory 704 can store electronic data that can be used by the electronic device 700. For example, the memory 704 can store electrical data or content such as, for example, audio and video files, documents and applications, device settings and user preferences, timing signals, control signals, and data structures or databases. The memory 704 can be configured as any type of memory. By way of example only, the memory 704 can be implemented as random access memory, read-only memory, Flash memory, removable memory, other types of storage elements, or combinations of such devices.

In various embodiments, the display 712 provides a graphical output, for example associated with an operating system, user interface, and/or applications of the electronic device 700. In one embodiment, the display 712 includes one or more sensors and is configured as a touch-sensitive (e.g., single-touch, multi-touch) and/or force-sensitive display to receive inputs from a user. For example, the display 712 may be integrated with a touch sensor (e.g., a capacitive touch sensor) and/or a force sensor to provide a touch- and/or force-sensitive display. The display 712 is operably coupled to the processing unit 702 of the electronic device 700.

The display 712 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 712 is positioned beneath and viewable through a cover that forms at least a portion of an enclosure of the electronic device 700.

In various embodiments, the input devices 706 may include any suitable components for detecting inputs. Examples of input devices 706 include audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 706 may be configured to detect one or more particular types of input and provide a signal (e.g., an input signal) corresponding to the detected input. The signal may be provided, for example, to the processing unit 702.

As discussed above, in some cases, the input device(s) 706 include a touch sensor (e.g., a capacitive touch sensor) integrated with the display 712 to provide a touch-sensitive display. Similarly, in some cases, the input device(s) 706 include a force sensor (e.g., a capacitive force sensor) integrated with the display 712 to provide a force-sensitive display.

The output devices 710 may include any suitable components for providing outputs. Examples of output devices 710 include audio output devices (e.g., speakers), visual output devices (e.g., lights or displays), tactile output devices (e.g., haptic output devices), communication devices (e.g., wired or wireless communication devices), and so on, or some combination thereof. Each output device 710 may be configured to receive one or more signals (e.g., an output signal provided by the processing unit 702) and provide an output corresponding to the signal.

In some cases, input devices 706 and output devices 710 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 702 may be operably coupled to the input devices 706 and the output devices 710. The processing unit 702 may be adapted to exchange signals with the input devices 706 and the output devices 710. For example, the processing unit 702 may receive an input signal from an input device 706 that corresponds to an input detected by the input device 706. The processing unit 702 may interpret the received input signal to determine whether to provide and/or change one or more outputs in response to the input signal. The processing unit 702 may then send an output signal to one or more of the output devices 710, to provide and/or change outputs as appropriate.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

As described above, one aspect of the present technology is determining electrocardiograms, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

What is claimed is:

1. An electronic watch comprising:
   a display;
   a cover over the display;
   an enclosure coupled to the cover and at least partially enclosing the display;
   a crown assembly comprising:
      an actuation member extending through an opening in the enclosure and comprising a knob positioned along an exterior side of the enclosure, the knob defining an input surface configured to receive a user input thereon;
a collapsible dome positioned at an end of the actuation member and configured to collapse in response to a translational input at the actuation member; and
a friction guard positioned between the end of the actuation member and the collapsible dome; and
a processing system within the enclosure and conductively coupled to the input surface of the knob via a conductive path extending through the collapsible dome, the friction guard, and the actuation member, the conductive path persisting when the collapsible dome is collapsed and when the collapsible dome is uncollapsed.

2. The electronic watch of claim 1, wherein:
the crown assembly further comprises a switch housing;
the collapsible dome is coupled to the switch housing; and
the crown assembly further comprises a conductive member at least partially encapsulated in the switch housing, the conductive path further extending through the conductive member.

3. The electronic watch of claim 2, wherein:
the conductive member is a first conductive member;
the first conductive member is conductively coupled to the collapsible dome when the collapsible dome is collapsed and when the collapsible dome is uncollapsed;
the crown assembly further comprises a second conductive member;
the collapsible dome is conductively coupled to the second conductive member when the collapsible dome is collapsed; and
the collapsible dome is conductively decoupled from the second conductive member when the collapsible dome is uncollapsed.

4. The electronic watch of claim 3, wherein the second conductive member is at least partially encapsulated in the switch housing.

5. The electronic watch of claim 1, wherein the processing system is configured to determine a biological parameter of a user based at least in part on a voltage detected at the input surface via the conductive path.

6. The electronic watch of claim 1, wherein the friction guard is configured to impart a biasing force to the actuation member to bias the actuation member towards an unactuated position.

7. The electronic watch of claim 6, wherein:
the biasing force is a first biasing force; and
the collapsible dome is configured to impart a second biasing force to the actuation member to bias the actuation member towards the unactuated position.

8. A wearable electronic device comprising:
an enclosure at least partially defining an internal volume;
an input assembly configured to receive a rotational input and a translational input and comprising:
a body portion external to the enclosure and defining an input surface; and
a shaft extending from the body portion through a hole defined in the enclosure;
a collapsible dome positioned in the internal volume and configured to transition from an uncollapsed state to a collapsed state in response to the translational input and configured to remain conductively coupled to the shaft when the collapsible dome is in the uncollapsed state and the collapsed state; and
a processing system within the internal volume and conductively coupled to the input surface via a conductive path through the collapsible dome, the shaft, and the body portion, the processing system configured to determine a biological parameter of a user based at least in part on a voltage detected at the input surface.

9. The wearable electronic device of claim 8, wherein the wearable electronic device is a watch.

10. The wearable electronic device of claim 8, wherein the wearable electronic device further comprises a friction guard defining an interposing portion positioned between the shaft and the collapsible dome.

11. The wearable electronic device of claim 10, wherein the friction guard conductively couples the shaft to the collapsible dome when the collapsible dome is in the uncollapsed state and the collapsed state.

12. The wearable electronic device of claim 10, wherein:
the wearable electronic device further comprises a switch housing positioned in the internal volume;
the collapsible dome is coupled to the switch housing; and
the friction guard is coupled to the switch housing.

13. The wearable electronic device of claim 12, further comprising a conductive member at least partially encapsulated in the switch housing and defining at least a portion of the conductive path.

14. The wearable electronic device of claim 12, wherein:
the friction guard further includes a flexure coupling the interposing portion to the switch housing;
the flexure is configured to impart a biasing force on the shaft via the interposing portion; and
the biasing force biases the input assembly towards an unactuated position.

15. A wearable electronic device comprising:
an enclosure;
an actuation member coupled to the enclosure and configured to receive a rotational input and a translational input, the actuation member comprising;
a knob external to the enclosure; and
a shaft coupled to the knob and extending through a hole defined in the enclosure;
a conductive dome positioned at an end of the shaft and configured to transition from an uncollapsed state to a collapsed state in response to a translational input applied to the knob; and
a friction guard positioned between the shaft and the conductive dome and conductively coupling the shaft to the conductive dome when the conductive dome is in the uncollapsed state and when the conductive dome is in the collapsed state.

16. The wearable electronic device of claim 15, further comprising a processing system at least partially within the enclosure and configured to determine a biological parameter of a user based at least in part on a voltage detected at an input surface of the knob via a conductive path extending through the knob, the shaft, the conductive dome, and the friction guard.

17. The wearable electronic device of claim 16, wherein the processing system is configured to determine the biological parameter when the conductive dome is in the collapsed state and when the conductive dome is in the uncollapsed state.

18. The wearable electronic device of claim 15, further comprising a switch housing at least partially within the enclosure and comprising:
a body; and
a conductive member coupled to the body and configured to conductively couple to the conductive dome when the conductive dome is in the collapsed state and when the conductive dome is in the uncollapsed state.

19. The wearable electronic device of claim 18, wherein:
the conductive member is a first conductive member;
the switch housing further comprises a second conductive member coupled to the body; and
the conductive dome is configured to conductively couple to the second conductive member in response to the collapse of the conductive dome.

20. The wearable electronic device of claim 19, wherein:
the switch housing further comprises a third conductive member coupled to the body and configured to conductively couple to the conductive dome when the conductive dome is in the collapsed state and when the conductive dome is in the uncollapsed state; and
a bias voltage is provided to the conductive dome via the third conductive member.

* * * * *